(12) United States Patent
Smits et al.

(10) Patent No.: US 9,598,369 B2
(45) Date of Patent: Mar. 21, 2017

(54) PROCESS FOR THE PREPARATION OF AMIDES FROM HINDERED ANILINES CONTAINING A PERHALOALKYL GROUP

(71) Applicant: Syngenta Participations AG, Basel (CH)

(72) Inventors: Helmars Smits, Stein (CH); Thomas Pitterna, Stein (CH); Ottmar Franz Hueter, Stein (CH); Andrew Edmunds, Stein (CH); Andre Stoller, Stein (CH); Pierre Joseph Marcel Jung, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/782,033

(22) PCT Filed: Apr. 1, 2014

(86) PCT No.: PCT/EP2014/056518
§ 371 (c)(1),
(2) Date: Oct. 2, 2015

(87) PCT Pub. No.: WO2014/161850
PCT Pub. Date: Oct. 9, 2014

(65) Prior Publication Data
US 2016/0168097 A1    Jun. 16, 2016

(30) Foreign Application Priority Data

Apr. 2, 2013 (EP) .................................... 13162011
Dec. 23, 2013 (EP) .................................... 13199385

(51) Int. Cl.
| | | |
|---|---|---|
| *C07D 211/78* | (2006.01) | |
| *C07D 211/90* | (2006.01) | |
| *C07D 213/81* | (2006.01) | |
| *C07C 255/57* | (2006.01) | |
| *C07C 233/15* | (2006.01) | |
| *C07C 253/30* | (2006.01) | |
| *C07D 213/82* | (2006.01) | |

(52) U.S. Cl.
CPC .......... *C07D 213/81* (2013.01); *C07C 233/15* (2013.01); *C07C 253/30* (2013.01); *C07C 255/57* (2013.01); *C07D 213/82* (2013.01)

(58) Field of Classification Search
None
See application file for complete search history.

(56) References Cited

U.S. PATENT DOCUMENTS 5,770,736 A    6/1998  Arya et al.

FOREIGN PATENT DOCUMENTS

| EP | 1714958 A1 | 10/2006 |
|---|---|---|
| WO | 2010/127928 A1 | 11/2010 |
| WO | WO 2010/127928 A1 * | 11/2010 |

OTHER PUBLICATIONS

International Search Report for International Patent Application No. PCT/EP2014/056518 mailed Jun. 20, 2014.

* cited by examiner

*Primary Examiner* — Noble Jarrell
*Assistant Examiner* — Ben S Michelson
(74) *Attorney, Agent, or Firm* — Brian D. McAlhaney

(57) ABSTRACT

The present invention provides a novel and improved process for the production of the production of hindered anilines containing perfluoroalky groups in good yield any by using close to stoichiometric amounts of acylating agent.

12 Claims, No Drawings

PROCESS FOR THE PREPARATION OF AMIDES FROM HINDERED ANILINES CONTAINING A PERHALOALKYL GROUP

RELATED APPLICATION INFORMATION

This application is a 371 of International Application No. PCT/EP2014/056518, filed 1 Apr. 2014, which claims priority to European Patent Application No. 13162011.4, filed 2 Apr. 2013, and European Patent Application No. 13199385.9 filed 23 Dec. 2013, the contents of all of which are incorporated herein by reference herein.

Hindered anilines containing perhaloalkyl groups are known to have low reactivity towards acylating agents. Standard methods of acylation such as treatment with acid chloride or anhydride in the presence of base and a nucleophilic catalyst proceed only in low yields, the major side reaction being double acylation. It is possible to obtain these amides in modest yield by using two equivalents of acylating agent followed by hydrolytic cleavage of one acyl group. However this method involves sacrificing at least one equivalent of often valuable acylating partner (see for example WO2008000438 and WO2010127928).

It is clear that a significant disadvantage of the prior art process is the sacrificial use of an excess acylating agent, which makes this process uneconomical and especially unsuitable for a large-scale production.

A method for enhancing the reactivity has now surprisingly been found that allows the preparation of the desired amides in good yield and by using close to stoichiometric amounts of acylating agent.

The aim of the present invention relates therefore to provide a novel and improved process for the acylation of hindered anilines containing perhaloalkyl groups.

Therefore the present invention relates to a process for the preparation of compounds of formula VI

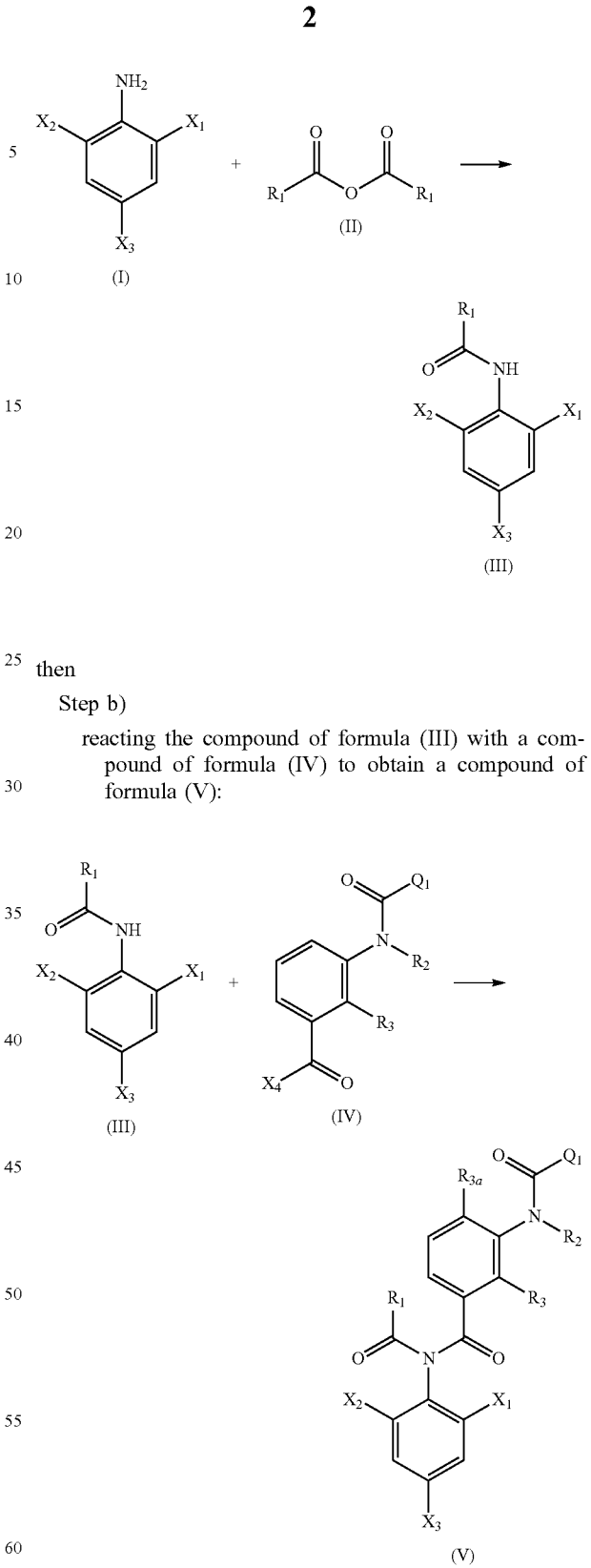

comprising at least the following steps a) to c):

Step a)
reacting a compound of formula (I) with a compound of formula (II) to obtain a compound of formula (III):

then
Step b)
reacting the compound of formula (III) with a compound of formula (IV) to obtain a compound of formula (V):

then
Step c)
reacting the compound of formula (V) with aqueous base to obtain a compound of formula (VI):

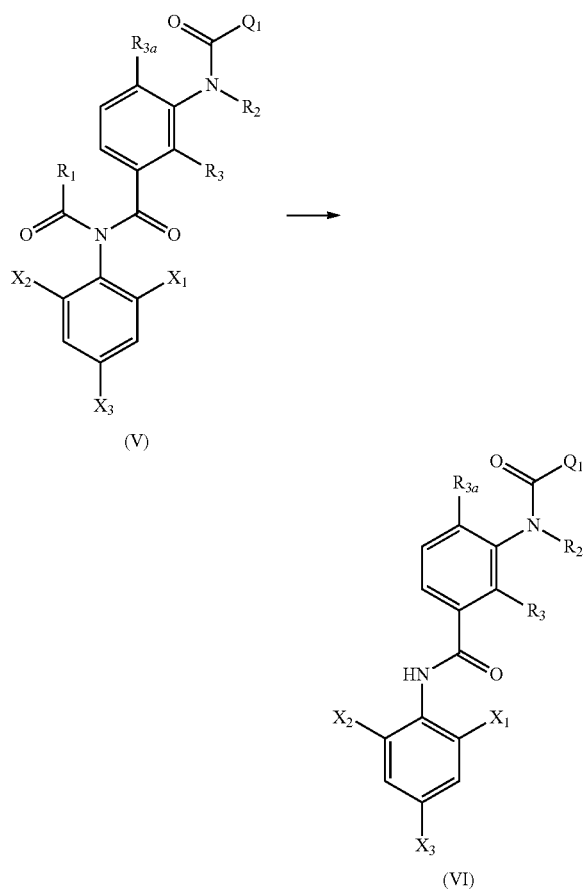

(V)

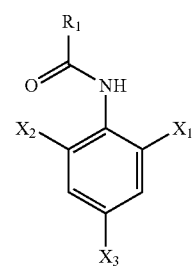

(VI)

wherein $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxymethyl, $C_1$-$C_4$-alkylsulphonyl, $C_1$-$C_4$-haloalkylsulphonyl, $C_1$-$C_4$-alkylsulphinyl, $C_1$-$C_4$-haloalkylsulphinyl, $C_1$-$C_4$-alkylthio, $C_1$-$C_4$-haloalkylthio, $X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;

$X_4$ is a leaving group selected from halogen, $C_1$-$C_6$-alkyl-C(O)O—, phenyl-C(O)O—, $C_1$-$C_6$-alkoxy-C(O)O—, phenoxy-C(O)O—, benzyloxy-C(O)O— and imidazol-1-yl;

$R_1$ is H, $C_1$-$C_4$ alkyl, $C_1$-$C_4$ haloalkyl;

$R_2$ is H or $C_1$-$C_4$-alkyl;

$R_3$ is H, fluorine, methoxy;

$R_{3a}$ is H or CN, $Q_1$ is 4-cyano-phenyl, 2-methyl-4-cyano-phenyl, 3-pyridyl or 4-pyridyl;

Preferably $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxymethyl, $C_1$-$C_4$-alkylsulphonyl, $C_1$-$C_4$-haloalkylsulphonyl, $C_1$-$C_4$-alkylsulphinyl, $C_1$-$C_4$-haloalkylsulphinyl, $C_1$-$C_4$-alkylthio, $C_1$-$C_4$-haloalkylthio, $X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;

$X_4$ is a leaving group selected from halogen, $C_1$-$C_6$-alkyl-C(O)O—, phenyl-C(O)O—, $C_1$-$C_6$-alkoxy-C(O)O—, phenoxy-C(O)O—, benzyloxy-C(O)O— and imidazol-1-yl;

$R_1$ is H, $C_1$-$C_4$ alkyl, $C_1$-$C_4$ haloalkyl;

$R_2$ is H or $C_1$-$C_4$-alkyl;

$R_3$ is H, fluorine, methoxy;

$R_{3a}$ is H or CN, $Q_1$ is 4-cyano-phenyl, 2-methyl-4-cyano-phenyl, 3-pyridyl or 4-pyridyl;

provided that $R_3$ is H when $R_{3a}$ is CN, and that $R_3$ is fluorine or methoxy when $R_{3a}$ is H;

More preferably $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxymethyl, $C_1$-$C_4$-alkylsulphonyl, $C_1$-$C_4$-haloalkylsulphonyl, $C_1$-$C_4$-alkylsulphinyl, $C_1$-$C_4$-haloalkylsulphinyl, $C_1$-$C_4$-alkylthio, $C_1$-$C_4$-haloalkylthio, $X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;

$X_4$ is a leaving group selected from halogen, $C_1$-$C_6$-alkyl-C(O)O—, phenyl-C(O)O—, $C_1$-$C_6$-alkoxy-C(O)O—, phenoxy-C(O)O—, benzyloxy-C(O)O— and imidazol-1-yl;

$R_1$ is H, $C_1$-$C_4$ alkyl, $C_1$-$C_4$ haloalkyl;

$R_2$ is H or $C_1$-$C_4$-alkyl;

$R_3$ is H, fluorine, methoxy;

$R_{3a}$ is H or CN, $Q_1$ is 4-cyano-phenyl, 2-methyl-4-cyano-phenyl, 3-pyridyl or 4-pyridyl;

provided that not both $R_3$ and $R_{3a}$ are H;

and provided that $R_3$ is H when $R_{3a}$ is CN, and that $R_3$ is fluorine or methoxy when $R_{3a}$ is H;

The above reaction steps are described in more detail below.

The present invention further relates to compounds according to formula (III)

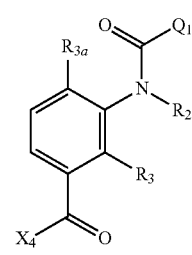

(III)

wherein $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxymethyl, $C_1$-$C_4$-alkylsulphonyl, $C_1$-$C_4$-haloalkylsulphonyl, $C_1$-$C_4$-alkylsulphinyl, $C_1$-$C_4$-haloalkylsulphinyl, $C_1$-$C_4$-alkylthio, $C_1$-$C_4$-haloalkylthio;

$X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;

$R_1$ is H, $C_1$-$C_4$ alkyl, $C_1$-$C_4$ haloalkyl;

The present invention further relates to compounds according to formula (IV)

(IV)

wherein $X_4$ is a leaving group selected from halogen, $C_1$-$C_6$-alkyl-C(O)O—, phenyl-C(O)O—, $C_1$-$C_6$-alkoxy-C(O)O—, phenoxy-C(O)O—, benzyloxy-C(O)O— and imidazol-1-yl;
$R_2$ is $C_1$-$C_4$-alkyl;
$R_3$ is H, fluorine or methoxy;
$R_{3a}$ is H or CN;
$Q_1$ is 2-methyl-4-cyano-phenyl, 3-pyridyl or 4-pyridyl;
provided that not both $R_3$ and $R_{3a}$ are H;

Preferably in the compounds according to formula (IV) $X_4$ is a leaving group selected from halogen, $C_1$-$C_6$-alkyl-C(O)O—, phenyl-C(O)O—, $C_1$-$C_6$-alkoxy-C(O)O—, phenoxy-C(O)O—, benzyloxy-C(O)O— and imidazol-1-yl;
$R_2$ is $C_1$-$C_4$-alkyl;
$R_3$ is H, fluorine or methoxy;
$R_{3a}$ is H or CN;
$Q_1$ is 2-methyl-4-cyano-phenyl, 3-pyridyl or 4-pyridyl;
provided that not both $R_3$ and $R_{3a}$ are H;
and provided that $R_3$ is H when $R_{3a}$ is CN, and that $R_3$ is fluorine or methoxy when $R_{3a}$ is H;

The present invention further relates to compounds according to formula (V)

wherein $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxymethyl, $C_1$-$C_4$-alkylsulphonyl, $C_1$-$C_4$-haloalkylsulphonyl, $C_1$-$C_4$-alkylsulphinyl, $C_1$-$C_4$-haloalkylsulphinyl, $C_1$-$C_4$-alkylthio, $C_1$-$C_4$-haloalkylthio,
$X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;
$R_1$ is H, $C_1$-$C_4$ alkyl, $C_1$-$C_4$ haloalkyl;
$R_2$ is H or $C_1$-$C_4$-alkyl;
$R_3$ is H, fluorine, methoxy;
$R_{3a}$ is H or CN,
provided that $R_3$ is H when $R_{3a}$ is CN;
$Q_1$ is 4-cyano-phenyl, 2-methyl-4-cyano-phenyl, 3-pyridyl or 4-pyridyl;

The compounds according to the invention, namely the compounds of formula (III), (IV) and (V), and the compounds mentioned in the method according to the invention may exist in different geometric or optical isomers or tautomeric forms.
This invention covers all such isomers and tautomers and mixtures thereof in all proportions as well as isotopic forms such as deuterated compounds.
The invention also covers salts of all compounds of the invention.

In particularly preferred embodiments for the methods and compounds of the invention (namely the compounds of formula (III), (IV) and (V)) and the compounds mentioned in the method according to the invention, the preferred groups for $X_1$, $X_2$, $X_3$, $X_4$, $R_1$, $R_2$, $R_3$, $R_{3a}$ and $Q_1$ in any combination thereof, are as set out below.
In one preferred embodiment $R_3$ is H, fluorine or methoxy
In one preferred embodiment $R_3$ is H;
In another preferred embodiment $R_3$ is fluorine;
In still another preferred embodiment $R_3$ is methoxy.
In one preferred embodiment $R_{3a}$ is H or cyano
In one preferred embodiment $R_{3a}$ is H;
In another preferred embodiment $R_{3a}$ is cyano;
In one preferred embodiment $R_3$ is H and $R_{3a}$ is H
In one preferred embodiment $R_3$ is fluorine and $R_{3a}$ is H
In one preferred embodiment $R_3$ is methoxy and $R_{3a}$ is H
In one preferred embodiment $R_3$ is H and $R_{3a}$ is CN
Preferably $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxymethyl;
More preferred $X_1$ and $X_2$ each independently are halogen, $C_1$-$C_4$ alkyl, $C_1$-$C_4$ haloalkyl, $C_1$-$C_4$ haloalkoxy;
Most preferred $X_1$ and $X_2$ each independently are halogen, methyl, ethyl, trifluoromethyl or difluoromethoxy.
Preferably $X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;
More preferred $X_3$ are heptafluoroprop-2-yl, 1-[chloro(difluoro)methyl]-1,2,2,2-tetrafluoro-ethyl or 1-[bromo(difluoro)methyl]-1,2,2,2-tetrafluoro-ethyl.
Even more preferred $X_3$ are heptafluoroprop-2-yl or 1-[bromo(difluoro)methyl]-1,2,2,2-tetrafluoro-ethyl.
Preferably $X_4$ is a leaving group selected from halogen, $C_1$-$C_6$-alkyl-C(O)O—, phenyl-C(O)O—, $C_1$-$C_6$-alkoxy-C(O)O—;
More preferred $X_4$ is a leaving group selected from halogen, $C_1$-$C_6$-alkyl-C(O)O—;
Even more preferred $X_4$ is a leaving group selected from halogen;
Most preferred $X_4$ is a chloride.
Preferably $R_1$ is H, $C_1$-$C_4$ alkyl;
More preferred $R_1$ is H, methyl;
Most preferred $R_1$ is methyl.
Preferably $R_2$ is H, methyl or ethyl;
More preferred $R_2$ is H or ethyl.
Preferably $Q_1$ is 4-cyano-phenyl, 2-methyl-4-cyano-phenyl or 4-pyridyl;
In a more preferred embodiment $Q_1$ is 2-methyl-4-cyano-phenyl or 4-pyridyl;
In a further more preferred embodiment $Q_1$ is 4-cyano-phenyl;
In an even more preferred embodiment $Q_1$ is 4-pyridyl;
In a further even more preferred embodiment $Q_1$ is 2-methyl-4-cyano-phenyl.
In one preferred embodiment (A) $R_3$ is H, fluorine or methoxy and $R_{3a}$ is H;
Preferably $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxymethyl;
More preferred $X_1$ and $X_2$ each independently are halogen, $C_1$-$C_4$ alkyl, $C_1$-$C_4$ haloalkyl, $C_1$-$C_4$ haloalkoxy;
Most preferred $X_1$ and $X_2$ each independently are halogen, methyl, ethyl, trifluoromethyl or difluoromethoxy.
Preferably $X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;

More preferred $X_3$ are heptafluoroprop-2-yl, 1-[chloro(difluoro)methyl]-1,2,2,2-tetrafluoro-ethyl or 1-[bromo(difluoro)methyl]-1,2,2,2-tetrafluoro-ethyl.

Even more preferred $X_3$ are heptafluoroprop-2-yl or 1-[bromo(difluoro)methyl]-1,2,2,2-tetrafluoro-ethyl.

Preferably $X_4$ is a leaving group selected from halogen, $C_1$-$C_6$-alkyl-C(O)O—, phenyl-C(O)O—, $C_1$-$C_6$-alkoxy-C(O)O—;

More preferred $X_4$ is a leaving group selected from halogen, $C_1$-$C_6$-alkyl-C(O)O—;

Even more preferred $X_4$ is a leaving group selected from halogen;

Most preferred $X_4$ is a chloride.

Preferably $R_1$ is H or $C_1$-$C_4$ alkyl;

More preferred $R_1$ is H or methyl;

Most preferred $R_1$ is methyl.

Preferably $R_2$ is methyl or ethyl;

More preferred $R_2$ is ethyl.

Preferably $Q_1$ is 4-cyano-phenyl or 4-pyridyl;

Further preferred $Q_1$ is 4-pyridyl;

Further preferred $Q_1$ is 4-cyano-phenyl

Further preferred $Q_1$ is 3-pyridyl or 4-pyridyl.

In one preferred embodiment (B) $R_3$ is H and $R_{3a}$ is H;

Preferably $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxymethyl;

More preferred $X_1$ and $X_2$ each independently are halogen, $C_1$-$C_4$ alkyl, $C_1$-$C_4$ haloalkyl, $C_1$-$C_4$ haloalkoxy;

Most preferred $X_1$ and $X_2$ each independently are halogen, methyl, ethyl, trifluoromethyl ordifluoromethoxy.

Preferably $X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;

More preferred $X_3$ are heptafluoroprop-2-yl, 1-[chloro(difluoro)methyl]-1,2,2,2-tetrafluoro-ethyl or 1-[bromo(difluoro)methyl]-1,2,2,2-tetrafluoro-ethyl.

Even more preferred $X_3$ are heptafluoroprop-2-yl or 1-[bromo(difluoro)methyl]-1,2,2,2-tetrafluoro-ethyl.

Preferably $X_4$ is a leaving group selected from halogen, $C_1$-$C_6$-alkyl-C(O)O—, phenyl-C(O)O—, $C_1$-$C_6$-alkoxy-C(O)O—;

More preferred $X_4$ is a leaving group selected from halogen, $C_1$-$C_6$-alkyl-C(O)O—;

Even more preferred $X_4$ is a leaving group selected from halogen;

Most preferred $X_4$ is a chloride.

Preferably $R_1$ is H or $C_1$-$C_4$ alkyl;

More preferred $R_1$ is H or methyl;

Most preferred $R_1$ is methyl.

Preferably $R_2$ is methyl or ethyl;

More preferred $R_2$ is ethyl.

Preferably $Q_1$ is 4-cyano-phenyl or 4-pyridyl;

Further preferred $Q_1$ is 4-pyridyl;

Further preferred $Q_1$ is 4-cyano-phenyl

Further preferred $Q_1$ is 3-pyridyl or 4-pyridyl;

In one preferred embodiment (C) $R_3$ is fluorine and $R_{3a}$ is H;

Preferably $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxymethyl;

More preferred $X_1$ and $X_2$ each independently are halogen, $C_1$-$C_4$ alkyl, $C_1$-$C_4$ haloalkyl or $C_1$-$C_4$ haloalkoxy;

Most preferred $X_1$ and $X_2$ each independently are halogen, methyl, ethyl, trifluoromethyl ordifluoromethoxy.

Preferably $X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;

More preferred $X_3$ are heptafluoroprop-2-yl, 1-[chloro(difluoro)methyl]-1,2,2,2-tetrafluoro-ethyl or 1-[bromo(difluoro)methyl]-1,2,2,2-tetrafluoro-ethyl.

Even more preferred $X_3$ are heptafluoroprop-2-yl or 1-[bromo(difluoro)methyl]-1,2,2,2-tetrafluoro-ethyl.

Preferably $X_4$ is a leaving group selected from halogen, $C_1$-$C_6$-alkyl-C(O)O—, phenyl-C(O)O—, $C_1$-$C_6$-alkoxy-C(O)O—;

More preferred $X_4$ is a leaving group selected from halogen, $C_1$-$C_6$-alkyl-C(O)O—;

Even more preferred $X_4$ is a leaving group selected from halogen;

Most preferred $X_4$ is a chloride.

Preferably $R_1$ is H or $C_1$-$C_4$ alkyl;

More preferred $R_1$ is H or methyl;

Most preferred $R_1$ is methyl.

Preferably $R_2$ is methyl or ethyl;

More preferred $R_2$ is ethyl.

Preferably $Q_1$ is 4-cyano-phenyl or 4-pyridyl;

Further preferred $Q_1$ is 4-pyridyl;

Further preferred $Q_1$ is 4-cyano-phenyl;

Further preferred $Q_1$ is 3-pyridyl or 4-pyridyl;

In one preferred embodiment (D) $R_3$ is methoxy and $R_{3a}$ is H;

Preferably $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy or $C_1$-$C_4$ alkoxymethyl;

More preferred $X_1$ and $X_2$ each independently are halogen, $C_1$-$C_4$ alkyl, $C_1$-$C_4$ haloalkyl or $C_1$-$C_4$ haloalkoxy;

Most preferred $X_1$ and $X_2$ each independently are halogen, methyl, ethyl, trifluoromethyl or difluoromethoxy.

Preferably $X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;

More preferred $X_3$ are heptafluoroprop-2-yl, 1-[chloro(difluoro)methyl]-1,2,2,2-tetrafluoro-ethyl or 1-[bromo(difluoro)methyl]-1,2,2,2-tetrafluoro-ethyl.

Even more preferred $X_3$ are heptafluoroprop-2-yl or 1-[bromo(difluoro)methyl]-1,2,2,2-tetrafluoro-ethyl.

Preferrably $X_4$ is a leaving group selected from halogen, $C_1$-$C_6$-alkyl-C(O)O—, phenyl-C(O)O—, $C_1$-$C_6$-alkoxy-C(O)O—;

More preferred $X_4$ is a leaving group selected from halogen, $C_1$-$C_6$-alkyl-C(O)O—;

Even more preferred $X_4$ is a leaving group selected from halogen;

Most preferred $X_4$ is a chloride.

Preferably $R_1$ is H or $C_1$-$C_4$ alkyl;

More preferred $R_1$ is H or methyl;

Most preferred $R_1$ is methyl.

Preferably $R_2$ is methyl or ethyl;

More preferred $R_2$ is ethyl.

Preferably $Q_1$ is 4-cyano-phenyl or 4-pyridyl;

Further preferred $Q_1$ is 4-pyridyl;

Further preferred $Q_1$ is 4-cyano-phenyl

Further preferred $Q_1$ is 3-pyridyl or 4-pyridyl;

In one preferred embodiment (E) $R_3$ is H and $R_{3a}$ is cyano;

Preferably $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy or $C_1$-$C_4$ alkoxymethyl;

More preferred $X_1$ and $X_2$ each independently are halogen, $C_1$-$C_4$ alkyl, $C_1$-$C_4$ haloalkyl or $C_1$-$C_4$ haloalkoxy;

Most preferred $X_1$ and $X_2$ each independently are halogen, methyl, ethyl, trifluoromethyl or difluoromethoxy.

Preferably $X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;

More preferred $X_3$ are heptafluoroprop-2-yl, 1-[chloro(difluoro)methyl]-1,2,2,2-tetrafluoro-ethyl or 1-[bromo(difluoro)methyl]-1,2,2,2-tetrafluoro-ethyl.

Even more preferred $X_3$ are heptafluoroprop-2-yl or 1-[bromo(difluoro)methyl]-1,2,2,2-tetrafluoro-ethyl.

Preferably $X_4$ is a leaving group selected from halogen, $C_1$-$C_6$-alkyl-C(O)O—, phenyl-C(O)O—, $C_1$-$C_6$-alkoxy-C(O)O—;

More preferred $X_4$ is a leaving group selected from halogen, $C_1$-$C_6$-alkyl-C(O)O—;

Even more preferred $X_4$ is a leaving group selected from halogen;

Most preferred $X_4$ is a chloride.

Preferably $R_1$ is H or $C_1$-$C_4$ alkyl;

More preferred $R_1$ is H or methyl;

Most preferred $R_1$ is methyl.

Preferably $R_2$ is methyl or ethyl;

More preferred $R_2$ is ethyl.

Preferably $Q_1$ is 4-cyano-phenyl or 4-pyridyl;

Further preferred $Q_1$ is 4-pyridyl;

Further preferred $Q_1$ is 4-cyano-phenyl

Further preferred $Q_1$ is 3-pyridyl or 4-pyridyl;

In a preferred embodiment (A) $Q_1$ is 4-cyano-phenyl or 4-pyridyl;

In a further preferred embodiment (A) $Q_1$ is 4-pyridyl;

In a further preferred embodiment (A) $Q_1$ is 4-cyano-phenyl;

In a further preferred embodiment (a) $Q_1$ is 3-pyridyl or 4-pyridyl;

In a preferred embodiment (B) $Q_1$ is 4-cyano-phenyl or 4-pyridyl;

In a further preferred embodiment (B) $Q_1$ is 4-pyridyl;

In a further preferred embodiment (B) $Q_1$ is 4-cyano-phenyl;

In a further preferred embodiment (B) $Q_1$ is 3-pyridyl or 4-pyridyl;

In a preferred embodiment (C) $Q_1$ is 4-cyano-phenyl or 4-pyridyl;

In a further preferred embodiment (C) $Q_1$ is 4-pyridyl;

In a further preferred embodiment (C) $Q_1$ is 4-cyano-phenyl;

In a further preferred embodiment (C) $Q_1$ is 3-pyridyl or 4-pyridyl;

In a preferred embodiment (D) $Q_1$ is 4-cyano-phenyl or 4-pyridyl;

In a further preferred embodiment (D) $Q_1$ is 4-pyridyl;

In a further preferred embodiment (D) $Q_1$ is 4-cyano-phenyl;

In a further preferred embodiment (D) $Q_1$ is 3-pyridyl or 4-pyridyl;

In a preferred embodiment (E) $Q_1$ is 4-cyano-phenyl or 4-pyridyl;

In a further preferred embodiment (E) $Q_1$ is 4-pyridyl;

In a further preferred embodiment (E) $Q_1$ is 4-cyano-phenyl;

In a further preferred embodiment (E) $Q_1$ is 3-pyridyl or 4-pyridyl;

Preferably $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy or $C_1$-$C_4$ alkoxymethyl;

$X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;

$X_4$ is a leaving group selected from halogen, $C_1$-$C_6$-alkyl-C(O)O—, phenyl-C(O)O—, $C_1$-$C_6$-alkoxy-C(O)O—;

$R_1$ is H or $C_1$-$C_4$ alkyl;

$R_2$ is methyl or ethyl;

$Q_1$ is 2-pyridyl or 4-pyridyl.

Equally preferably $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxymethyl, $X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;

$X_4$ is a leaving group selected from halogen, $C_1$-$C_6$-alkyl-C(O)O—, phenyl-C(O)O—, $C_1$-$C_6$-alkoxy-C(O)O—;

$R_1$ is H, $C_1$-$C_4$ alkyl, $R_2$ is methyl or ethyl $Q_1$ is 4-cyano-phenyl, 3-pyridyl or 4-pyridyl;

More preferred $X_1$ and $X_2$ each independently are halogen, $C_1$-$C_4$ alkyl, $C_1$-$C_4$ haloalkyl, $C_1$-$C_4$ haloalkoxy;

$X_3$ is heptafluoroprop-2-yl;

$X_4$ is a leaving group selected from halogen, $C_1$-$C_6$-alkyl-C(O)O—;

$R_1$ is H or methyl;

$R_2$ is ethyl;

$Q_1$ is 4-pyridyl.

More preferred $X_1$ and $X_2$ each independently are halogen, $C_1$-$C_4$ alkyl, $C_1$-$C_4$ haloalkyl, $C_1$-$C_4$ haloalkoxy, $X_3$ is 1-[chloro(difluoro)methyl]-1,2,2,2-tetrafluoro-ethyl;

$X_4$ is a leaving group selected from halogen, $C_1$-$C_6$-alkyl-C(O)O—;

$R_1$ is H, methyl, $R_2$ is ethyl $Q_1$ is 4-pyridyl;

More preferred $X_1$ and $X_2$ each independently are halogen, $C_1$-$C_4$ alkyl, $C_1$-$C_4$ haloalkyl, $C_1$-$C_4$ haloalkoxy, $X_3$ is 1-[bromo(difluoro)methyl]-1,2,2,2-tetrafluoro-ethyl;

$X_4$ is a leaving group selected from halogen, $C_1$-$C_6$-alkyl-C(O)O—;

$R_1$ is H, methyl, $R_2$ is ethyl $Q_1$ is 4-pyridyl;

More preferred $X_1$ and $X_2$ each independently are halogen, $C_1$-$C_4$ alkyl, $C_1$-$C_4$ haloalkyl, $C_1$-$C_4$ haloalkoxy, $X_3$ is nonafluorobut-2-yl;

$X_4$ is a leaving group selected from halogen, $C_1$-$C_6$-alkyl-C(O)O—;

$R_1$ is H, methyl, $R_2$ is ethyl $Q_1$ is 4-pyridyl;

More preferred $R_3$ is methoxy; and $R_{3a}$ is H,

More preferred $R_3$ is fluorine; and $R_{3a}$ is H,

More preferred $R_3$ is H; and $R_{3a}$ is CN,

More preferred $R_3$ is H; $R_{3a}$ is H,

The following schemes describe the reactions of the invention in more detail. The substituent definitions are the same as defined previously:

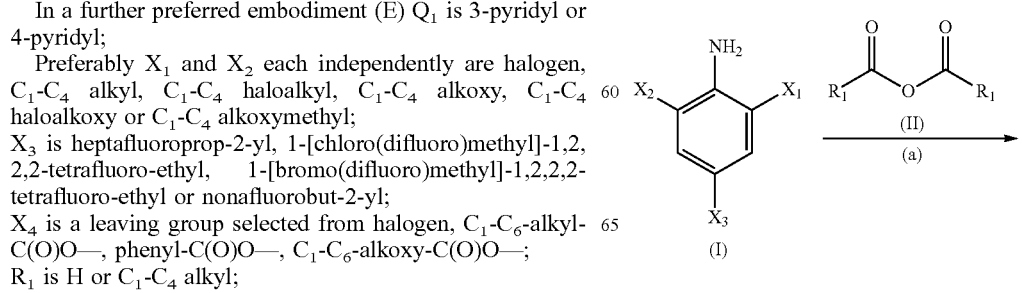

Scheme 1

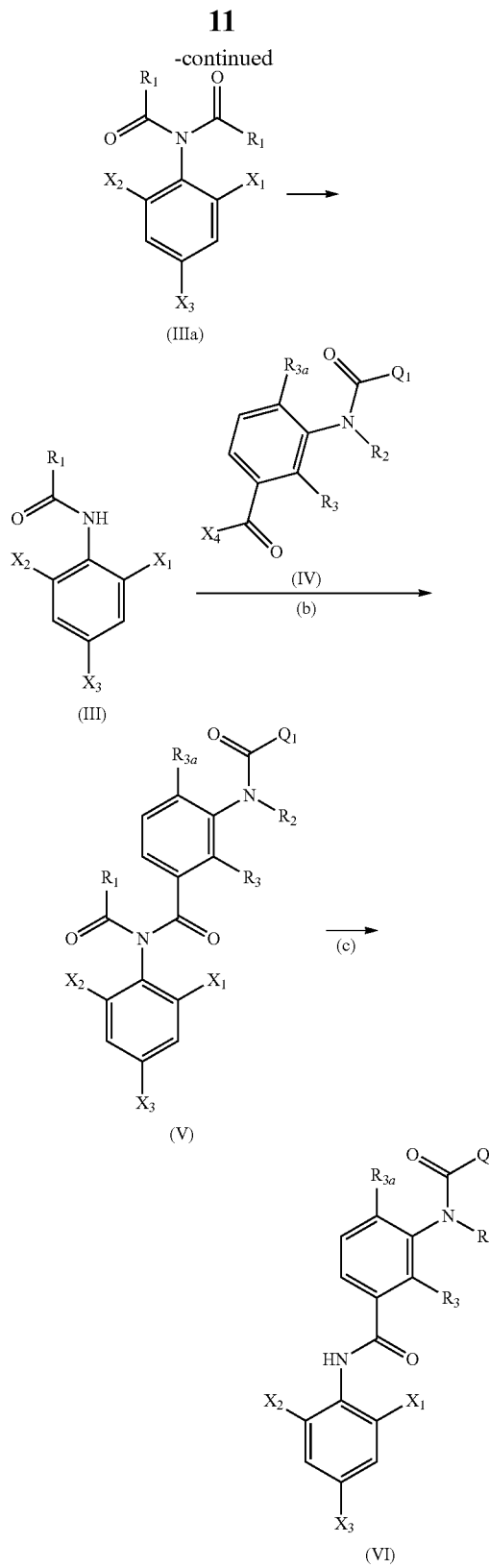

Step a)

Compounds of formula (III) can be prepared by reacting compounds of formula (I) with compounds of formula (II).

The reactions of compounds of formula (I) with compounds of formula (II) are preferably carried out in the presence of a suitable base. Suitable bases include, but are not limited to carbonates such as $Na_2CO_3$, $K_2CO_3$, hydroxides such as NaOH, nitrogen-based organic bases such as amines, pyridines and derivatives thereof, e.g. triethylamine, tri-n-propylamine, pyridine and diisopropylethylamine. The reactions of compounds of formula (I) with compounds of formula (II) are preferably carried out in the presence of a solvent. Suitable solvents include, but are not limited to organic solvents such as toluene, chloroform, dichloromethane, dichloroethane, monochlorobenzene, dichlorobenzene, trichlorobenzene, 4-fluorotoluene, THF, dioxane, preferably chloroform, dichloromethane. It is also possible to conduct the reaction in a biphasic mixture of an organic solvent and water.

The reaction can be carried out at a temperature from −20° C. to 100° C., preferably from 0° C. to 30° C. (e.g. greater than −20° C., preferably greater than 0° C., e.g. lower than 100° C., preferably lower than 30° C.).

The reactions of compounds of formula (I) and (II) are preferably carried out in the presence of a catalyst. Suitable catalysts include, but are not limited to nucleophilic catalysts capable of promoting acyl transfer reactions such as 4-dialkylaminopyridines, N-alkylimidazoles, phosphines, imidazolylidene carbenes, 1,2-diamines, bicyclic amidines, isothioureas and guanidines, triazoles, some alcohols, iodide and cyanide salts, preferably 4-dimethylaminopyridine.

Alternatively the reaction can be carried out in the presence of a catalytic amount of a suitable acid. Suitable acids include but are not limited to mineral acids such as sulfuric acid, hydrochloric acid and organic acids such as trifluoroacetic acid.

The reactions of compounds of (I) and (II) are carried out either by using compound of formula (II) as the solvent or in the presence of suitable additional organic solvent. Suitable solvents include but are not limited to dichloromethane, dichloroethane, THF and dioxane.

The reaction can be carried out at a temperature from 0° C. to 120° C., preferably from 30° C. to 100° C. (e.g. greater than 0° C., preferably greater than 30° C., e.g. lower than 120° C., preferably lower than 70° C.).

The reaction between compounds of formula (I) and compounds of formula (II) can be carried out under acidic conditions to yield compounds of formula III. Compounds of formula III can be formed by hydrolysis of intermediate compounds of formula IIIa. It is thus preferable to treat the resulting mixture of compounds of formula (III) and diacylated intermediate (IIIa) obtained in step a, with a suitable aqueous base. Suitable bases include, but are not limited to, aqueous solutions of NaOH, LiOH, $Na_2CO_3$, or $K_2CO_3$. Suitable organic co-solvents include, but are not limited to, THF and dioxane.

Step b)

Compounds of formula (V) can be prepared by reacting compounds of formula (III) with compounds of formula (IV).

The reactions of compounds of formula (III) with compounds of formula (IV) are preferably carried out in the presence of a suitable base. Suitable bases include, but are not limited to, carbonates such as $Na_2CO_3$, $K_2CO_3$, hydroxides such as NaOH, nitrogen-based organic bases such as amines, pyridines and derivatives thereof, e.g. triethylamine, tri-n-propylamine, pyridine and diisopropylethylamine. The reactions of compounds of formula (III) with compounds of formula (IV) are preferably carried out in the presence of a solvent. Suitable solvents include, but are not limited to organic solvents such as toluene, chloroform, dichloromethane, dichloroethane, monochlorobenzene, dichlorobenzene, trichlorobenzene, 4-fluorotoluene, THF, or dioxane, preferably chloroform ordichloromethane. It is also possible to conduct the reaction in a biphasic mixture of an organic solvent and water.

The reaction can be carried out at a temperature from −20° C. to 100° C., preferably from 0° C. to 30° C. (e.g. greater than −20° C., preferably greater than 0° C., e.g. lower than 100° C., preferably lower than 30° C.).

The reactions of compounds of formula (III) and (IV) could be carried out in the presence of a catalyst. Suitable catalysts include, but are not limited to nucleophilic catalysts capable of promoting acyl transfer reactions such as 4-dialkylaminopyridines, N-alkylimidazoles, phosphines, imidazolylidene carbenes, 1,2-diamines, bicyclic amidines, isothioureas and guanidines, triazoles, some alcohols, iodide and cyanide salts, preferably 4-dimethylaminopyridine.

Step c)

Compounds of formula (VI) can be prepared by reacting compounds of formula (V) with a suitable base. Suitable bases include but are not limited to aqueous solutions of NaOH, LiOH or $K_2CO_3$. The reactions of compounds of formula (VI) with an aqueous base are preferably carried out in the presence of a suitable organic co-solvent. Suitable solvents include, but are not limited to, THF, dioxane and ethanol.

The reaction can be carried out at a temperature from −20° C. to 100° C., preferably from 0° C. to 30° C. (e.g. greater than −20° C., preferably greater than 0° C., e.g. lower than 100° C., preferably lower than 30° C.).

Alternatively the compounds of formula (VI) can be prepared in a one pot process by reacting compounds of formula (III) with compounds of formula (IV) as described for step b, followed by addition of a suitable aqueous base.

Suitable bases include, but are not limited to LiOH, NaOH, KOH, $Na_2CO_3$, $K_2CO_3$.

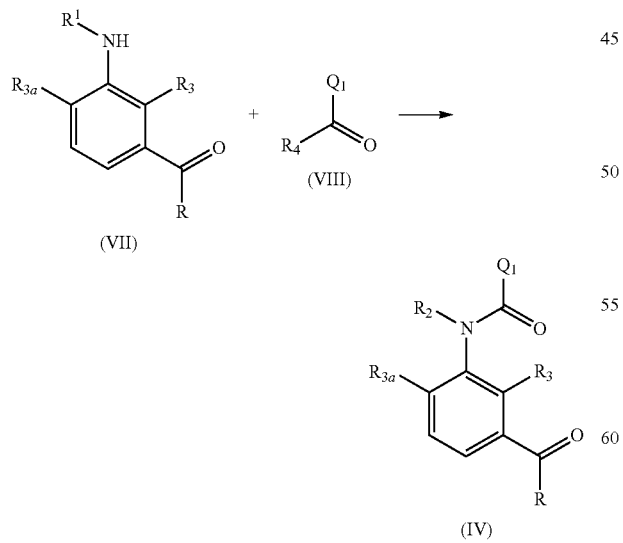

1) Acid halides of formula (IV), wherein R is Cl, F or Br, may be made from carboxylic acids of formula (IV),
wherein R is OH by treatment with thionyl chloride, oxalyl chloride or phosgene.

2) Carboxylic acids of formula (IV), wherein R is OH, may be formed from esters of formula (IV), wherein R is $C_1$-$C_6$alkoxy by treatment of the ester with an alkali hydroxide, such as lithium hydroxide, in a solvent, such as a mixture of THF and water.

3) Esters of formula (IV), wherein R is $C_1$-$C_6$alkoxy, may be made by reacting compounds of formula (VII), wherein R is $C_1$-$C_6$alkoxy, by acylation with a carboxylic acid of formula (VIII) wherein $R_4$ is OH or with acid halide of formula (VIII) wherein $R_4$ is Cl, F or Br. When $R_4$ is OH such reactions may be carried out in the presence of a coupling reagent, such as DCC (N,N'-dicyclohexyl-carbodiimide), EDC (1-ethyl-3-[3-dimethylamino-propyl]carbodiimide hydrochloride) or BOP-Cl (bis(2-oxo-3-oxazolidinyl)phosphonic chloride), in the presence of a base, such as pyridine, triethylamine, 4-(dimethylamino)pyridine or diisopropylethylamine, and optionally in the presence of a nucleophilic catalyst, such as hydroxybenzotriazole. When $R_4$ is Cl, such reactions may be carried out under basic conditions, for example in the presence of pyridine, triethylamine, 4-(dimethylamino)pyridine or diisopropylethylamine, and optionally in the presence of a nucleophilic catalyst. Alternatively, the reaction may be conducted in a biphasic system comprising an organic solvent, preferably ethyl acetate, and an aqueous solvent, preferably a solution of sodium bicarbonate. When $R_4$ is $C_1$-$C_6$alkoxy the ester may be converted directly to the amide by heating the ester and amine together in a thermal process.

4) Compounds of formula (VII), wherein R is $C_1$-$C_6$alkoxy, may be made from compounds of formula (IX) by sequential treatment with an alcohol R—OH under acidic conditions and then formation of the N—$R^1$ bond. For example, reductive amination may be achieved by treatment of the amine with an aldehyde or ketone and a reducing agent such as sodium cyanoborohydride. Alternatively, alkylation may be achieved by treating the amine with an alkylating agent such as an alkyl halide, optionally in the presence of a base.

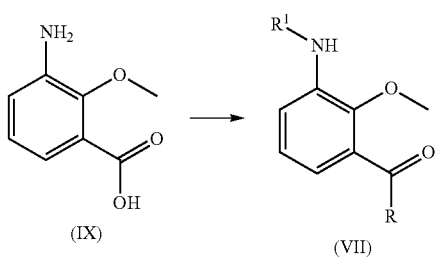

R = $C_1$-$C_6$-Alkoxy

6) Alternatively, compounds of formula (VII), wherein R is $C_1$-$C_6$alkoxy, may be made from a compound of formula (X), wherein R is $C_1$-$C_6$alkoxy and LG is a leaving group, such as fluoro, chloro or sulfonate, via the displacement of the leaving group by an amine of formula $R^1$—$NH_2$ or other imine analogue followed by hydrolysis with a metal catalyst. See, for example: Chemical Communications (2009), (14), 1891-1893 or Journal of Organic Chemistry (2000), 65(8), 2612-2614.

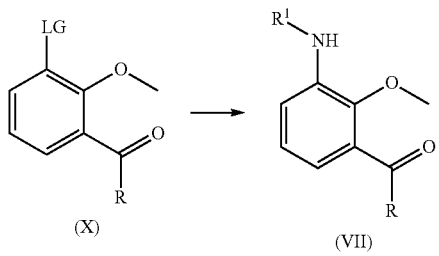

Compounds of formula (X) and amines of formula $R^1$—$NH_2$ are either known compounds or may be made by methods known to a person skilled in the art.

6a) Alternatively, compounds of formula (VII), wherein R is $C_1$-$C_6$alkoxy, may be made from a compounds of formula (XI), wherein R is $C_1$-$C_6$alkoxy via reduction in the presence of a metal catalyst and a suitable two carbon building block such as acetaldehyde or acetonitrile. See for example: J. Org. Chem. 2007, 72, 9815 or Org. Lett. 2005, 7, 471

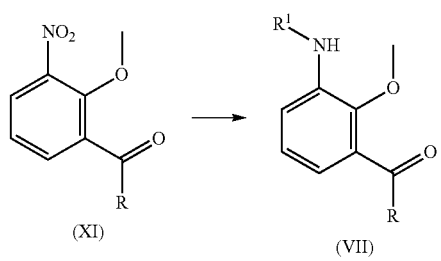

The following Examples illustrate, but do not limit, the invention.

TABLE A

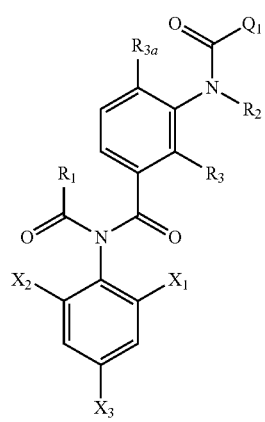

(V)

| Line n° | $X_3$ | $R_1$ | $R_2$ | $R_3$ | $R_{3a}$ | $Q_1$ |
|---|---|---|---|---|---|---|
| A.1 | heptafluoroprop-2-yl | H | Me | H | H | 3-Pyridyl |
| A.2 | nonafluorobut-2-yl | H | Me | H | H | 3-Pyridyl |
| A.3 | heptafluoroprop-2-yl | Me | Me | H | H | 3-Pyridyl |
| A.4 | nonafluorobut-2-yl | Me | Me | H | H | 3-Pyridyl |
| A.5 | heptafluoroprop-2-yl | H | Et | H | H | 3-Pyridyl |
| A.6 | nonafluorobut-2-yl | H | Et | H | H | 3-Pyridyl |
| A.7 | heptafluoroprop-2-yl | Me | Et | H | H | 3-Pyridyl |
| A.8 | nonafluorobut-2-yl | Me | Et | H | H | 3-Pyridyl |
| A.9 | heptafluoroprop-2-yl | H | Me | F | H | 3-Pyridyl |
| A.10 | nonafluorobut-2-yl | H | Me | F | H | 3-Pyridyl |
| A.11 | heptafluoroprop-2-yl | Me | Me | F | H | 3-Pyridyl |
| A.12 | nonafluorobut-2-yl | Me | Me | F | H | 3-Pyridyl |
| A.13 | heptafluoroprop-2-yl | H | Et | F | H | 3-Pyridyl |
| A.14 | nonafluorobut-2-yl | H | Et | F | H | 3-Pyridyl |
| A.15 | heptafluoroprop-2-yl | Me | Et | F | H | 3-Pyridyl |
| A.16 | nonafluorobut-2-yl | Me | Et | F | H | 3-Pyridyl |
| A.17 | heptafluoroprop-2-yl | H | Me | $OCH_3$ | H | 3-Pyridyl |
| A.18 | nonafluorobut-2-yl | H | Me | $OCH_3$ | H | 3-Pyridyl |
| A.19 | heptafluoroprop-2-yl | Me | Me | $OCH_3$ | H | 3-Pyridyl |
| A.20 | nonafluorobut-2-yl | Me | Me | $OCH_3$ | H | 3-Pyridyl |
| A.21 | heptafluoroprop-2-yl | H | Et | $OCH_3$ | H | 3-Pyridyl |
| A.22 | nonafluorobut-2-yl | H | Et | $OCH_3$ | H | 3-Pyridyl |
| A.23 | heptafluoroprop-2-yl | Me | Et | $OCH_3$ | H | 3-Pyridyl |
| A.24 | nonafluorobut-2-yl | Me | Et | $OCH_3$ | H | 3-Pyridyl |
| A.25 | 1-[chloro(difluoro)methyl]-1,2,2,2-tetrafluoro-ethyl | H | Me | H | H | 4-Pyridyl |
| A.26 | 1-[bromo(difluoro)methyl]-1,2,2,2-tetrafluoro-ethyl | H | Me | H | H | 4-Pyridyl |
| A.27 | 1-[chloro(difluoro)methyl]-1,2,2,2-tetrafluoro-ethyl | Me | Me | H | H | 4-Pyridyl |
| A.28 | 1-[bromo(difluoro)methyl]-1,2,2,2-tetrafluoro-ethyl | Me | Me | H | H | 4-Pyridyl |
| A.29 | 1-[chloro(difluoro)methyl]-1,2,2,2-tetrafluoro-ethyl | H | Et | H | H | 4-Pyridyl |
| A.30 | 1-[bromo(difluoro)methyl]-1,2,2,2-tetrafluoro-ethyl | H | Et | H | H | 4-Pyridyl |
| A.31 | 1-[chloro(difluoro)methyl]-1,2,2,2-tetrafluoro-ethyl | Me | Et | H | H | 4-Pyridyl |
| A.32 | 1-[bromo(difluoro)methyl]-1,2,2,2-tetrafluoro-ethyl | Me | Et | H | H | 4-Pyridyl |
| A.33 | 1-[chloro(difluoro)methyl]-1,2,2,2-tetrafluoro-ethyl | H | H | H | H | 4-Pyridyl |

TABLE A-continued (V)

| Line n° | X₃ | R₁ | R₂ | R₃ | R₃ₐ | Q₁ |
|---|---|---|---|---|---|---|
| A.34 | 1-[bromo(difluoro)methyl]-1,2,2,2-tetrafluoro-ethyl | H | H | H | H | 4-Pyridyl |
| A.35 | 1-[chloro(difluoro)methyl]-1,2,2,2-tetrafluoro-ethyl | Me | H | H | H | 4-Pyridyl |
| A.36 | 1-[bromo(difluoro)methyl]-1,2,2,2-tetrafluoro-ethyl | Me | H | H | H | 4-Pyridyl |
| A.37 | 1-[chloro(difluoro)methyl]-1,2,2,2-tetrafluoro-ethyl | H | Me | F | H | 4-Pyridyl |
| A.38 | 1-[bromo(difluoro)methyl]-1,2,2,2-tetrafluoro-ethyl | H | Me | F | H | 4-Pyridyl |
| A.39 | 1-[chloro(difluoro)methyl]-1,2,2,2-tetrafluoro-ethyl | Me | Me | F | H | 4-Pyridyl |
| A.40 | 1-[bromo(difluoro)methyl]-1,2,2,2-tetrafluoro-ethyl | Me | Me | F | H | 4-Pyridyl |
| A.41 | 1-[chloro(difluoro)methyl]-1,2,2,2-tetrafluoro-ethyl | H | Et | F | H | 4-Pyridyl |
| A.42 | 1-[bromo(difluoro)methyl]-1,2,2,2-tetrafluoro-ethyl | H | Et | F | H | 4-Pyridyl |
| A.43 | 1-[chloro(difluoro)methyl]-1,2,2,2-tetrafluoro-ethyl | Me | Et | F | H | 4-Pyridyl |
| A.44 | 1-[bromo(difluoro)methyl]-1,2,2,2-tetrafluoro-ethyl | Me | Et | F | H | 4-Pyridyl |
| A.45 | 1-[chloro(difluoro)methyl]-1,2,2,2-tetrafluoro-ethyl | H | H | F | H | 4-Pyridyl |
| A.46 | 1-[bromo(difluoro)methyl]-1,2,2,2-tetrafluoro-ethyl | H | H | F | H | 4-Pyridyl |
| A.47 | 1-[chloro(difluoro)methyl]-1,2,2,2-tetrafluoro-ethyl | Me | H | F | H | 4-Pyridyl |
| A.48 | 1-[bromo(difluoro)methyl]-1,2,2,2-tetrafluoro-ethyl | Me | H | F | H | 4-Pyridyl |
| A.49 | 1-[chloro(difluoro)methyl]-1,2,2,2-tetrafluoro-ethyl | H | Me | OCH₃ | H | 4-Pyridyl |
| A.50 | 1-[bromo(difluoro)methyl]-1,2,2,2-tetrafluoro-ethyl | H | Me | OCH₃ | H | 4-Pyridyl |
| A.51 | 1-[chloro(difluoro)methyl]-1,2,2,2-tetrafluoro-ethyl | Me | Me | OCH₃ | H | 4-Pyridyl |
| A.52 | 1-[bromo(difluoro)methyl]-1,2,2,2-tetrafluoro-ethyl | Me | Me | OCH₃ | H | 4-Pyridyl |
| A.53 | 1-[chloro(difluoro)methyl]-1,2,2,2-tetrafluoro-ethyl | H | Et | OCH₃ | H | 4-Pyridyl |
| A.54 | 1-[bromo(difluoro)methyl]-1,2,2,2-tetrafluoro-ethyl | H | Et | OCH₃ | H | 4-Pyridyl |
| A.55 | 1-[chloro(difluoro)methyl]-1,2,2,2-tetrafluoro-ethyl | Me | Et | OCH₃ | H | 4-Pyridyl |
| A.56 | 1-[bromo(difluoro)methyl]-1,2,2,2-tetrafluoro-ethyl | Me | Et | OCH₃ | H | 4-Pyridyl |
| A.57 | 1-[chloro(difluoro)methyl]-1,2,2,2-tetrafluoro-ethyl | H | H | OCH₃ | H | 4-Pyridyl |
| A.58 | 1-[bromo(difluoro)methyl]-1,2,2,2-tetrafluoro-ethyl | H | H | OCH₃ | H | 4-Pyridyl |
| A.59 | 1-[chloro(difluoro)methyl]-1,2,2,2-tetrafluoro-ethyl | Me | H | OCH₃ | H | 4-Pyridyl |
| A.60 | 1-[bromo(difluoro)methyl]-1,2,2,2-tetrafluoro-ethyl | Me | H | OCH₃ | H | 4-Pyridyl |
| A.61 | heptafluoroprop-2-yl | H | Me | H | H | 4-Pyridyl |
| A.62 | nonafluorobut-2-yl | H | Me | H | H | 4-Pyridyl |
| A.63 | heptafluoroprop-2-yl | Me | Me | H | H | 4-Pyridyl |
| A.64 | nonafluorobut-2-yl | Me | Me | H | H | 4-Pyridyl |
| A.65 | heptafluoroprop-2-yl | H | Et | H | H | 4-Pyridyl |
| A.66 | nonafluorobut-2-yl | H | Et | H | H | 4-Pyridyl |
| A.67 | heptafluoroprop-2-yl | Me | Et | H | H | 4-Pyridyl |
| A.68 | nonafluorobut-2-yl | Me | Et | H | H | 4-Pyridyl |
| A.69 | heptafluoroprop-2-yl | H | H | H | H | 4-Pyridyl |
| A.70 | nonafluorobut-2-yl | H | H | H | H | 4-Pyridyl |
| A.71 | heptafluoroprop-2-yl | Me | H | H | H | 4-Pyridyl |
| A.72 | nonafluorobut-2-yl | Me | H | H | H | 4-Pyridyl |
| A.73 | heptafluoroprop-2-yl | H | Me | F | H | 4-Pyridyl |
| A.74 | nonafluorobut-2-yl | H | Me | F | H | 4-Pyridyl |
| A.75 | heptafluoroprop-2-yl | Me | Me | F | H | 4-Pyridyl |
| A.76 | nonafluorobut-2-yl | Me | Me | F | H | 4-Pyridyl |
| A.77 | heptafluoroprop-2-yl | H | Et | F | H | 4-Pyridyl |
| A.78 | nonafluorobut-2-yl | H | Et | F | H | 4-Pyridyl |
| A.79 | heptafluoroprop-2-yl | Me | Et | F | H | 4-Pyridyl |
| A.80 | nonafluorobut-2-yl | Me | Et | F | H | 4-Pyridyl |
| A.81 | heptafluoroprop-2-yl | H | H | F | H | 4-Pyridyl |
| A.82 | nonafluorobut-2-yl | H | H | F | H | 4-Pyridyl |
| A.83 | heptafluoroprop-2-yl | Me | H | F | H | 4-Pyridyl |
| A.84 | nonafluorobut-2-yl | Me | H | F | H | 4-Pyridyl |
| A.85 | heptafluoroprop-2-yl | H | Me | OCH₃ | H | 4-Pyridyl |
| A.86 | nonafluorobut-2-yl | H | Me | OCH₃ | H | 4-Pyridyl |
| A.87 | heptafluoroprop-2-yl | Me | Me | OCH₃ | H | 4-Pyridyl |
| A.88 | nonafluorobut-2-yl | Me | Me | OCH₃ | H | 4-Pyridyl |
| A.89 | heptafluoroprop-2-yl | H | Et | OCH₃ | H | 4-Pyridyl |

TABLE A-continued (V)

| Line n° | X₃ | R₁ | R₂ | R₃ | R₃ₐ | Q₁ |
|---|---|---|---|---|---|---|
| A.90 | nonafluorobut-2-yl | H | Et | OCH₃ | H | 4-Pyridyl |
| A.91 | heptafluoroprop-2-yl | Me | Et | OCH₃ | H | 4-Pyridyl |
| A.92 | nonafluorobut-2-yl | Me | Et | OCH₃ | H | 4-Pyridyl |
| A.93 | heptafluoroprop-2-yl | H | H | OCH₃ | H | 4-Pyridyl |
| A.94 | nonafluorobut-2-yl | H | H | OCH₃ | H | 4-Pyridyl |
| A.95 | heptafluoroprop-2-yl | Me | H | OCH₃ | H | 4-Pyridyl |
| A.96 | nonafluorobut-2-yl | Me | H | OCH₃ | H | 4-Pyridyl |
| A.97 | heptafluoroprop-2-yl | H | Me | H | H | 4-cyanophenyl |
| A.98 | nonafluorobut-2-yl | H | Me | H | H | 4-cyanophenyl |
| A.99 | heptafluoroprop-2-yl | Me | Me | H | H | 4-cyanophenyl |
| A.100 | nonafluorobut-2-yl | Me | Me | H | H | 4-cyanophenyl |
| A.101 | heptafluoroprop-2-yl | H | Et | H | H | 4-cyanophenyl |
| A.102 | nonafluorobut-2-yl | H | Et | H | H | 4-cyanophenyl |
| A.103 | heptafluoroprop-2-yl | Me | Et | H | H | 4-cyanophenyl |
| A.104 | nonafluorobut-2-yl | Me | Et | H | H | 4-cyanophenyl |
| A.105 | heptafluoroprop-2-yl | H | Me | F | H | 4-cyanophenyl |
| A.106 | nonafluorobut-2-yl | H | Me | F | H | 4-cyanophenyl |
| A.107 | heptafluoroprop-2-yl | Me | Me | F | H | 4-cyanophenyl |
| A.108 | nonafluorobut-2-yl | Me | Me | F | H | 4-cyanophenyl |
| A.109 | heptafluoroprop-2-yl | H | Et | F | H | 4-cyanophenyl |
| A.110 | nonafluorobut-2-yl | H | Et | F | H | 4-cyanophenyl |
| A.111 | heptafluoroprop-2-yl | Me | Et | F | H | 4-cyanophenyl |
| A.112 | nonafluorobut-2-yl | Me | Et | F | H | 4-cyanophenyl |
| A.113 | heptafluoroprop-2-yl | H | Me | OCH₃ | H | 4-cyanophenyl |
| A.114 | nonafluorobut-2-yl | H | Me | OCH₃ | H | 4-cyanophenyl |
| A.115 | heptafluoroprop-2-yl | Me | Me | OCH₃ | H | 4-cyanophenyl |
| A.116 | nonafluorobut-2-yl | Me | Me | OCH₃ | H | 4-cyanophenyl |
| A.117 | heptafluoroprop-2-yl | H | Et | OCH₃ | H | 4-cyanophenyl |
| A.118 | nonafluorobut-2-yl | H | Et | OCH₃ | H | 4-cyanophenyl |
| A.119 | heptafluoroprop-2-yl | Me | Et | OCH₃ | H | 4-cyanophenyl |
| A.120 | nonafluorobut-2-yl | Me | Et | OCH₃ | H | 4-cyanophenyl |
| A.121 | heptafluoroprop-2-yl | H | Me | H | H | 2-methyl-4-cyano-phenyl |
| A.122 | nonafluorobut-2-yl | H | Me | H | H | 2-methyl-4-cyano-phenyl |
| A.123 | heptafluoroprop-2-yl | Me | Me | H | H | 2-methyl-4-cyano-phenyl |
| A.124 | nonafluorobut-2-yl | Me | Me | H | H | 2-methyl-4-cyano-phenyl |
| A.125 | heptafluoroprop-2-yl | H | Et | H | H | 2-methyl-4-cyano-phenyl |
| A.126 | nonafluorobut-2-yl | H | Et | H | H | 2-methyl-4-cyano-phenyl |
| A.127 | heptafluoroprop-2-yl | Me | Et | H | H | 2-methyl-4-cyano-phenyl |
| A.128 | nonafluorobut-2-yl | Me | Et | H | H | 2-methyl-4-cyano-phenyl |
| A.129 | heptafluoroprop-2-yl | H | Me | F | H | 2-methyl-4-cyano-phenyl |
| A.130 | nonafluorobut-2-yl | H | Me | F | H | 2-methyl-4-cyano-phenyl |
| A.131 | heptafluoroprop-2-yl | Me | Me | F | H | 2-methyl-4-cyano-phenyl |
| A.132 | nonafluorobut-2-yl | Me | Me | F | H | 2-methyl-4-cyano-phenyl |
| A.133 | heptafluoroprop-2-yl | H | Et | F | H | 2-methyl-4-cyano-phenyl |
| A.134 | nonafluorobut-2-yl | H | Et | F | H | 2-methyl-4-cyano-phenyl |
| A.135 | heptafluoroprop-2-yl | Me | Et | F | H | 2-methyl-4-cyano-phenyl |
| A.136 | nonafluorobut-2-yl | Me | Et | F | H | 2-methyl-4-cyano-phenyl |
| A.137 | heptafluoroprop-2-yl | H | Me | OCH₃ | H | 2-methyl-4-cyano-phenyl |
| A.138 | nonafluorobut-2-yl | H | Me | OCH₃ | H | 2-methyl-4-cyano-phenyl |
| A.139 | heptafluoroprop-2-yl | Me | Me | OCH₃ | H | 2-methyl-4-cyano-phenyl |
| A.140 | nonafluorobut-2-yl | Me | Me | OCH₃ | H | 2-methyl-4-cyano-phenyl |
| A.141 | heptafluoroprop-2-yl | H | Et | OCH₃ | H | 2-methyl-4-cyano-phenyl |
| A.142 | nonafluorobut-2-yl | H | Et | OCH₃ | H | 2-methyl-4-cyano-phenyl |
| A.143 | heptafluoroprop-2-yl | Me | Et | OCH₃ | H | 2-methyl-4-cyano-phenyl |
| A.144 | nonafluorobut-2-yl | Me | Et | OCH₃ | H | 2-methyl-4-cyano-phenyl |
| A.145 | heptafluoroprop-2-yl | H | Me | H | CN | 2-methyl-4-cyano-phenyl |

TABLE A-continued

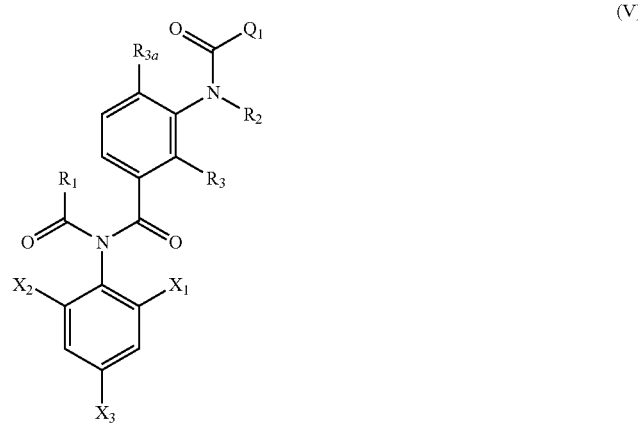

(V)

| Line n° | $X_3$ | $R_1$ | $R_2$ | $R_3$ | $R_{3a}$ | $Q_1$ |
|---|---|---|---|---|---|---|
| A.146 | nonafluorobut-2-yl | H | Me | H | CN | 2-methyl-4-cyano-phenyl |
| A.147 | heptafluoroprop-2-yl | Me | Me | H | CN | 2-methyl-4-cyano-phenyl |
| A.148 | nonafluorobut-2-yl | Me | Me | H | CN | 2-methyl-4-cyano-phenyl |
| A.149 | heptafluoroprop-2-yl | H | Et | H | CN | 2-methyl-4-cyano-phenyl |
| A.150 | nonafluorobut-2-yl | H | Et | H | CN | 2-methyl-4-cyano-phenyl |
| A.151 | heptafluoroprop-2-yl | Me | Et | H | CN | 2-methyl-4-cyano-phenyl |
| A.152 | nonafluorobut-2-yl | Me | Et | H | CN | 2-methyl-4-cyano-phenyl |
| A.153 | heptafluoroprop-2-yl | H | H | H | CN | 2-methyl-4-cyano-phenyl |
| A.154 | nonafluorobut-2-yl | H | H | H | CN | 2-methyl-4-cyano-phenyl |
| A.155 | heptafluoroprop-2-yl | Me | H | H | CN | 2-methyl-4-cyano-phenyl |
| A.156 | nonafluorobut-2-yl | Me | H | H | CN | 2-methyl-4-cyano-phenyl |

Table 1:
Compounds of the formula (V) wherein $X_1$ is Cl, $X_2$ is Cl and the combination of the substituents $X_3$, $R_1$, $R_2$, $R_3$ and $Q_1$ for each compound corresponds to a line A.1 to A.156 of Table A.

Table 2:
Compounds of the formula (V) wherein $X_1$ is Br, $X_2$ is Cl and the combination of the substituents $X_3$, $R_1$, $R_2$, $R_3$ and $Q_1$ for each compound corresponds to a line A.1 to A.156 of Table A.

Table 3:
Compounds of the formula (V) wherein $X_1$ is I, $X_2$ is Cl and the combination of the substituents $X_3$, $R_1$, $R_2$, $R_3$ and $Q_1$ for each compound corresponds to a line A.1 to A.156 of Table A.

Table 4:
Compounds of the formula (V) wherein $X_1$ is methyl, $X_2$ is Cl and the combination of the substituents $X_3$, $R_1$, $R_2$, $R_3$ and $Q_1$ for each compound corresponds to a line A.1 to A.156 of Table A.

Table 5:
Compounds of the formula (V) wherein $X_1$ is ethyl, $X_2$ is Cl and the combination of the substituents $X_3$, $R_1$, $R_2$, $R_3$ and $Q_1$ for each compound corresponds to a line A.1 to A.156 of Table A.

Table 6:
Compounds of the formula (V) wherein $X_1$ is trifluoromethyl, $X_2$ is Cl and the combination of the substituents $X_3$, $R_1$, $R_2$, $R_3$ and $Q_1$ for each compound corresponds to a line A.1 to A.156 of Table A.

Table 7:
Compounds of the formula (V) wherein $X_1$ is trifluoromethoxy, $X_2$ is Cl and the combination of the substituents $X_3$, $R_1$, $R_2$, $R_3$ and $Q_1$ for each compound corresponds to a line A.1 to A.156 of Table A.

Table 8:
Compounds of the formula (V) wherein $X_1$ is difluoromethoxy, $X_2$ is Cl and the combination of the substituents $X_3$, $R_1$, $R_2$, $R_3$ and $Q_1$ for each compound corresponds to a line A.1 to A.156 of Table A.

Table 9:
Compounds of the formula (V) wherein $X_1$ is trifluoromethylthio, $X_2$ is Cl and the combination of the substituents $X_3$, $R_1$, $R_2$, $R_3$ and $Q_1$ for each compound corresponds to a line A.1 to A.156 of Table A.

Table 10:
Compounds of the formula (V) wherein $X_1$ is trifluoromethylsulfinyl, $X_2$ is Cl and the combination of the substituents $X_3$, $R_1$, $R_2$, $R_3$ and $Q_1$ for each compound corresponds to a line A.1 to A.156 of Table A.

Table 11:
Compounds of the formula (V) wherein $X_1$ is Br, $X_2$ is Br and the combination of the substituents $X_3$, $R_1$, $R_2$, $R_3$ and $Q_1$ for each compound corresponds to a line A.1 to A.156 of Table A.

Table 12:
Compounds of the formula (V) wherein $X_1$ is I, $X_2$ is Br and the combination of the substituents $X_3$, $R_1$, $R_2$, $R_3$ and $Q_1$ for each compound corresponds to a line A.1 to A.156 of Table A.

Table 13:
Compounds of the formula (V) wherein $X_1$ is methyl, $X_2$ is Br and the combination of the substituents $X_3$, $R_1$, $R_2$, $R_3$ and $Q_1$ for each compound corresponds to a line A.1 to A.156 of Table A.

Table 14:
Compounds of the formula (V) wherein $X_1$ is ethyl, $X_2$ is Br and the combination of the substituents $X_3$, $R_1$, $R_2$, $R_3$ and $Q_1$ for each compound corresponds to a line A.1 to A.156 of Table A.

Table 15:
Compounds of the formula (V) wherein $X_1$ is trifluoromethyl, $X_2$ is Br and the combination of the substituents $X_3$, $R_1$, $R_2$, $R_3$ and $Q_1$ for each compound corresponds to a line A.1 to A.156 of Table A.

Table 16:
Compounds of the formula (V) wherein $X_1$ is trifluoromethoxy, $X_2$ is Br and the combination of the substituents $X_3$, $R_1$, $R_2$, $R_3$ and $Q_1$ for each compound corresponds to a line A.1 to A.156 of Table A.

Table 17:
Compounds of the formula (V) wherein $X_1$ is difluoromethoxy, $X_2$ is Br and the combination of the substituents $X_3$, $R_1$, $R_2$, $R_3$ and $Q_1$ for each compound corresponds to a line A.1 to A.156 of Table A.

Table 18:
Compounds of the formula (V) wherein $X_1$ is trifluoromethylthio, $X_2$ is Br and the combination of the substituents $X_3$, $R_1$, $R_2$, $R_3$ and $Q_1$ for each compound corresponds to a line A.1 to A.156 of Table A.

Table 19:
Compounds of the formula (V) wherein $X_1$ is trifluoromethylsulfinyl, $X_2$ is Br and the combination of the substituents $X_3$, $R_1$, $R_2$, $R_3$ and $Q_1$ for each compound corresponds to a line A.1 to A.156 of Table A.

Table 20:
Compounds of the formula (V) wherein $X_1$ is I, $X_2$ is I and the combination of the substituents $X_3$, $R_1$, $R_2$, $R_3$ and $Q_1$ for each compound corresponds to a line A.1 to A.156 of Table A.

Table 21:
Compounds of the formula (V) wherein $X_1$ is methyl, $X_2$ is I and the combination of the substituents $X_3$, $R_1$, $R_2$, $R_3$ and $Q_1$ for each compound corresponds to a line A.1 to A.156 of Table A.

Table 22:
Compounds of the formula (V) wherein $X_1$ is ethyl, $X_2$ is I and the combination of the substituents $X_3$, $R_1$, $R_2$, $R_3$ and $Q_1$ for each compound corresponds to a line A.1 to A.156 of Table A.

Table 23:
Compounds of the formula (V) wherein $X_1$ is trifluoromethyl, $X_2$ is I and the combination of the substituents $X_3$, $R_1$, $R_2$, $R_3$ and $Q_1$ for each compound corresponds to a line A.1 to A.156 of Table A.

Table 24:
Compounds of the formula (V) wherein $X_1$ is trifluoromethoxy, $X_2$ is I and the combination of the substituents $X_3$, $R_1$, $R_2$, $R_3$ and $Q_1$ for each compound corresponds to a line A.1 to A.156 of Table A.

Table 25:
Compounds of the formula (V) wherein $X_1$ is difluoromethoxy, $X_2$ is I and the combination of the substituents $X_3$, $R_1$, $R_2$, $R_3$ and $Q_1$ for each compound corresponds to a line A.1 to A.156 of Table A.

Table 26:
Compounds of the formula (V) wherein $X_1$ is trifluoromethylthio, $X_2$ is I and the combination of the substituents $X_3$, $R_1$, $R_2$, $R_3$ and $Q_1$ for each compound corresponds to a line A.1 to A.156 of Table A.

Table 27:
Compounds of the formula (V) wherein $X_1$ is trifluoromethylsulfinyl, $X_2$ is I and the combination of the substituents $X_3$, $R_1$, $R_2$, $R_3$ and $Q_1$ for each compound corresponds to a line A.1 to A.156 of Table A.

Table 28:
Compounds of the formula (V) wherein $X_1$ is methyl, $X_2$ is methyl and the combination of the substituents $X_3$, $R_1$, $R_2$, $R_3$ and $Q_1$ for each compound corresponds to a line A.1 to A.156 of Table A.

Table 29:
Compounds of the formula (V) wherein $X_1$ is ethyl, $X_2$ is methyl and the combination of the substituents $X_3$, $R_1$, $R_2$, $R_3$ and $Q_1$ for each compound corresponds to a line A.1 to A.156 of Table A.

Table 30:
Compounds of the formula (V) wherein $X_1$ is trifluoromethyl, $X_2$ is methyl and the combination of the substituents $X_3$, $R_1$, $R_2$, $R_3$ and $Q_1$ for each compound corresponds to a line A.1 to A.156 of Table A.

Table 31:
Compounds of the formula (V) wherein $X_1$ is trifluoromethoxy, $X_2$ is methyl and the combination of the substituents $X_3$, $R_1$, $R_2$, $R_3$ and $Q_1$ for each compound corresponds to a line A.1 to A.156 of Table A.

Table 32:
Compounds of the formula (V) wherein $X_1$ is difluoromethoxy, $X_2$ is methyl and the combination of the substituents $X_3$, $R_1$, $R_2$, $R_3$ and $Q_1$ for each compound corresponds to a line A.1 to A.156 of Table A.

Table 33:
Compounds of the formula (V) wherein $X_1$ is trifluoromethylthio, $X_2$ is methyl and the combination of the substituents $X_3$, $R_1$, $R_2$, $R_3$ and $Q_1$ for each compound corresponds to a line A.1 to A.156 of Table A.

Table 34:
Compounds of the formula (V) wherein $X_1$ is trifluoromethylsulfinyl, $X_2$ is methyl and the combination of the substituents $X_3$, $R_1$, $R_2$, $R_3$ and $Q_1$ for each compound corresponds to a line A.1 to A.156 of Table A.

Table 35:
Compounds of the formula (V) wherein $X_1$ is ethyl, $X_2$ is ethyl and the combination of the substituents $X_3$, $R_1$, $R_2$, $R_3$ and $Q_1$ for each compound corresponds to a line A.1 to A.156 of Table A.

Table 36:
Compounds of the formula (V) wherein $X_1$ is trifluoromethyl, $X_2$ is ethyl and the combination of the substituents $X_3$, $R_1$, $R_2$, $R_3$ and $Q_1$ for each compound corresponds to a line A.1 to A.156 of Table A.

Table 37:
Compounds of the formula (V) wherein $X_1$ is trifluoromethoxy, $X_2$ is ethyl and the combination of the substituents $X_3$, $R_1$, $R_2$, $R_3$ and $Q_1$ for each compound corresponds to a line A.1 to A.156 of Table A.

Table 38:
Compounds of the formula (V) wherein $X_1$ is difluoromethoxy, $X_2$ is ethyl and the combination of the substituents $X_3$, $R_1$, $R_2$, $R_3$ and $Q_1$ for each compound corresponds to a line A.1 to A.156 of Table A.

Table 39:
Compounds of the formula (V) wherein $X_1$ is trifluoromethylthio, $X_2$ is ethyl and the combination of the substituents $X_3$, $R_1$, $R_2$, $R_3$ and $Q_1$ for each compound corresponds to a line A.1 to A.156 of Table A.

Table 40:
Compounds of the formula (V) wherein $X_1$ is trifluoromethylsulfinyl, $X_2$ is ethyl and the combination of the substituents $X_3$, $R_1$, $R_2$, $R_3$ and $Q_1$ for each compound corresponds to a line A.1 to A.156 of Table A.

Table 41:
Compounds of the formula (V) wherein $X_1$ is trifluoromethyl, $X_2$ is trifluoromethyl and the combination of the substituents $X_3$, $R_1$, $R_2$, $R_3$ and $Q_1$ for each compound corresponds to a line A.1 to A.156 of Table A.

Table 42:
Compounds of the formula (V) wherein $X_1$ is trifluoromethoxy, $X_2$ is trifluoromethyl and the combination of the substituents $X_3$, $R_1$, $R_2$, $R_3$ and $Q_1$ for each compound corresponds to a line A.1 to A.156 of Table A.

Table 43:
Compounds of the formula (V) wherein $X_1$ is difluoromethoxy, $X_2$ is trifluoromethyl and the combination of the substituents $X_3$, $R_1$, $R_2$, $R_3$ and $Q_1$ for each compound corresponds to a line A.1 to A.156 of Table A.

Table 44:
Compounds of the formula (V) wherein $X_1$ is trifluoromethylthio, $X_2$ is trifluoromethyl and the combination of the substituents $X_3$, $R_1$, $R_2$, $R_3$ and $Q_1$ for each compound corresponds to a line A.1 to A.156 of Table A.

Table 45:
Compounds of the formula (V) wherein $X_1$ is trifluoromethylsulfinyl, $X_2$ is trifluoromethyl and the combination of the substituents $X_3$, $R_1$, $R_2$, $R_3$ and $Q_1$ for each compound corresponds to a line A.1 to A.156 of Table A.

Table 46:
Compounds of the formula (V) wherein $X_1$ is trifluoromethoxy, $X_2$ is trifluoromethoxy and the combination of the substituents $X_3$, $R_1$, $R_2$, $R_3$ and $Q_1$ for each compound corresponds to a line A.1 to A.156 of Table A.

Table 47:
Compounds of the formula (V) wherein $X_1$ is difluoromethoxy, $X_2$ is trifluoromethoxy and the combination of the substituents $X_3$, $R_1$, $R_2$, $R_3$ and $Q_1$ for each compound corresponds to a line A.1 to A.156 of Table A.

Table 48:
Compounds of the formula (V) wherein $X_1$ is trifluoromethylthio, $X_2$ is trifluoromethoxy and the combination of the substituents $X_3$, $R_1$, $R_2$, $R_3$ and $Q_1$ for each compound corresponds to a line A.1 to A.156 of Table A.

Table 49:
Compounds of the formula (V) wherein $X_1$ is trifluoromethylsulfinyl, $X_2$ is trifluoromethoxy and the combination of the substituents $X_3$, $R_1$, $R_2$, $R_3$ and $Q_1$ for each compound corresponds to a line A.1 to A.156 of Table A.

Table 50:
Compounds of the formula (V) wherein $X_1$ is difluoromethoxy, $X_2$ is difluoromethoxy and the combination of the substituents $X_3$, $R_1$, $R_2$, $R_3$ and $Q_1$ for each compound corresponds to a line A.1 to A.156 of Table A.

Table 51:
Compounds of the formula (V) wherein $X_1$ is trifluoromethylthio, $X_2$ is difluoromethoxy and the combination of the substituents $X_3$, $R_1$, $R_2$, $R_3$ and $Q_1$ for each compound corresponds to a line A.1 to A.156 of Table A.

Table 52:
Compounds of the formula (V) wherein $X_1$ is trifluoromethylsulfinyl, $X_2$ is difluoromethoxy and the combination of the substituents $X_3$, $R_1$, $R_2$, $R_3$ and $Q_1$ for each compound corresponds to a line A.1 to A.156 of Table A.

Table 53:
Compounds of the formula (V) wherein $X_1$ is trifluoromethylthio, $X_2$ is trifluoromethylthio and the combination of the substituents $X_3$, $R_1$, $R_2$, $R_3$ and $Q_1$ for each compound corresponds to a line A.1 to A.156 of Table A.

Table 54:
Compounds of the formula (V) wherein $X_1$ is trifluoromethylsulfinyl, $X_2$ is trifluoromethylthio and the combination of the substituents $X_3$, $R_1$, $R_2$, $R_3$ and $Q_1$ for each compound corresponds to a line A.1 to A.156 of Table A.

Table 55:
Compounds of the formula (V) wherein $X_1$ is trifluoromethylsulfinyl, $X_2$ is trifluoromethylsulfinyl and the combination of the substituents $X_3$, $R_1$, $R_2$, $R_3$ and $Q_1$ for each compound corresponds to a line A.1 to A.156 of Table A.

TABLE B

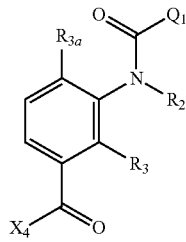

(IV)

| Line n° | $R_2$ | $R_3$ | $R_{3a}$ | $Q_1$ |
|---|---|---|---|---|
| B.1 | Me | H | H | 3-Pyridyl |
| B.2 | Et | H | H | 3-Pyridyl |
| B.3 | Me | F | H | 3-Pyridyl |
| B.4 | Et | F | H | 3-Pyridyl |
| B.5 | Me | OCH$_3$ | H | 3-Pyridyl |
| B.6 | Et | OCH$_3$ | H | 3-Pyridyl |
| B.7 | Me | H | H | 4-Pyridyl |
| B.8 | Et | H | H | 4-Pyridyl |
| B.9 | Me | F | H | 4-Pyridyl |
| B.10 | Et | F | H | 4-Pyridyl |
| B.11 | Me | OCH$_3$ | H | 4-Pyridyl |
| B.12 | Et | OCH$_3$ | H | 4-Pyridyl |
| B.13 | Me | H | H | 2-methyl-4-cyano-phenyl |
| B.14 | Et | H | H | 2-methyl-4-cyano-phenyl |
| B.15 | Me | F | H | 2-methyl-4-cyano-phenyl |
| B.16 | Et | F | H | 2-methyl-4-cyano-phenyl |
| B.17 | Me | OCH$_3$ | H | 2-methyl-4-cyano-phenyl |
| B.18 | Et | OCH$_3$ | H | 2-methyl-4-cyano-phenyl |
| B.19 | Me | H | CN | 2-methyl-4-cyano-phenyl |
| B.20 | Et | H | CN | 2-methyl-4-cyano-phenyl |

Table 56:
Compounds of the formula (IV) wherein $X_4$ is Cl and the combination of the substituents $R_2$, $R_3$ and $Q_1$ for each compound corresponds to a line B.1 to B.20 of Table B.

Table 57:
Compounds of the formula (IV) wherein $X_4$ is F and the combination of the substituents $R_2$, $R_3$ and $Q_1$ for each compound corresponds to a line B.1 to B.20 of Table B.

Table 58:
Compounds of the formula (IV) wherein $X_4$ is Br and the combination of the substituents $R_2$, $R_3$ and $Q_1$ for each compound corresponds to a line B.1 to B.20 of Table B.

Table 59:
Compounds of the formula (IV) wherein $X_4$ is I and the combination of the substituents $R_2$, $R_3$ and $Q_1$ for each compound corresponds to a line B.1 to B.20 of Table B.

Table 60:
Compounds of the formula (IV) wherein $X_4$ is acetoxy and the combination of the substituents $R_2$, $R_3$ and $Q_1$ for each compound corresponds to a line B.1 to B.20 of Table B.

Table 61:
Compounds of the formula (IV) wherein $X_4$ is formyloxy and the combination of the substituents $R_2$, $R_3$ and $Q_1$ for each compound corresponds to a line B.1 to B.20 of Table B.

Table 62:
Compounds of the formula (IV) wherein $X_4$ is benzoyloxy and the combination of the substituents $R_2$, $R_3$ and $Q_1$ for each compound corresponds to a line B.1 to B.20 of Table B.

Table 63:

Compounds of the formula (IV) wherein $X_4$ is methoxycarbonyloxy and the combination of the substituents $R_2$, $R_3$ and $Q_1$ for each compound corresponds to a line B.1 to B.20 of Table B.

Table 64:

Compounds of the formula (IV) wherein $X_4$ is ethoxycarbonyloxy and the combination of the substituents $R_2$, $R_3$ and $Q_1$ for each compound corresponds to a line B.1 to B.20 of Table B.

Table 65:

Compounds of the formula (IV) wherein $X_4$ is isopropoxycarbonyloxy and the combination of the substituents $R_2$, $R_3$ and $Q_1$ for each compound corresponds to a line B.1 to B.20 of Table B.

Table 66:

Compounds of the formula (IV) wherein $X_4$ is phenoxycarbonyloxy and the combination of the substituents $R_2$, $R_3$ and $Q_1$ for each compound corresponds to a line B.1 to B.20 of Table B.

Table 67:

Compounds of the formula (IV) wherein $X_4$ is benzyloxycarbonyloxy and the combination of the substituents $R_2$, $R_3$ and $Q_1$ for each compound corresponds to a line B.1 to B.20 of Table B.

Table 68:

Compounds of the formula (IV) wherein $X_4$ is imidazol-1-yl and the combination of the substituents $R_2$, $R_3$ and $Q_1$ for each compound corresponds to a line B.1 to B.20 of Table B.

TABLE C

| Line n° | $X_1$ | $X_2$ |
|---|---|---|
| C.1 | Cl | Cl |
| C.2 | Br | Cl |
| C.3 | I | Cl |
| C.4 | Me | Cl |
| C.5 | Et | Cl |
| C.6 | $CF_3$ | Cl |
| C.7 | $OCF_3$ | Cl |
| C.8 | $OCHF_2$ | Cl |
| C.9 | $SCF_3$ | Cl |
| C.10 | $S(O)CF_3$ | Cl |
| C.11 | Br | Br |
| C.12 | I | Br |
| C.13 | Me | Br |
| C.14 | Et | Br |
| C.15 | $CF_3$ | Br |
| C.16 | $OCF_3$ | Br |
| C.17 | $OCHF_2$ | Br |
| C.18 | $SCF_3$ | Br |
| C.19 | $S(O)CF_3$ | Br |
| C.20 | I | I |
| C.21 | Me | I |
| C.22 | Et | I |
| C.23 | $CF_3$ | I |
| C.24 | $OCF_3$ | I |
| C.25 | $OCHF_2$ | I |
| C.26 | $SCF_3$ | I |
| C.27 | $S(O)CF_3$ | I |
| C.28 | Me | Me |
| C.29 | Et | Me |
| C.30 | $CF_3$ | Me |
| C.31 | $OCF_3$ | Me |
| C.32 | $OCHF_2$ | Me |
| C.33 | $SCF_3$ | Me |
| C.34 | $S(O)CF_3$ | Me |
| C.35 | Et | Et |
| C.36 | $CF_3$ | Et |
| C.37 | $OCF_3$ | Et |
| C.38 | $OCHF_2$ | Et |
| C.39 | $SCF_3$ | Et |
| C.40 | $S(O)CF_3$ | Et |
| C.41 | $CF_3$ | $CF_3$ |
| C.42 | $OCF_3$ | $CF_3$ |
| C.43 | $OCHF_2$ | $CF_3$ |
| C.44 | $SCF_3$ | $CF_3$ |
| C.45 | $S(O)CF_3$ | $CF_3$ |
| C.46 | $OCF_3$ | $OCF_3$ |
| C.47 | $OCHF_2$ | $OCF_3$ |
| C.48 | $SCF_3$ | $OCF_3$ |
| C.49 | $S(O)CF_3$ | $OCF_3$ |
| C.50 | $OCHF_2$ | $OCHF_2$ |
| C.51 | $SCF_3$ | $OCHF_2$ |
| C.52 | $S(O)CF_3$ | $OCHF_2$ |
| C.53 | $SCF_3$ | $SCF_3$ |
| C.54 | $S(O)CF_3$ | $SCF_3$ |
| C.55 | $S(O)CF_3$ | $S(O)CF_3$ |

Table 69:

Compounds of the formula (III) wherein $X_3$ is heptafluoroprop-2-yl, $R_1$ is H and the combination of the substituents $X_1$ and $X_2$ for each compound corresponds to a line C.1 to C.55 of Table C.

Table 70:

Compounds of the formula (III) wherein $X_3$ is heptafluoroprop-2-yl, $R_1$ is methyl and the combination of the substituents $X_1$ and $X_2$ for each compound corresponds to a line C.1 to C.55 of Table C.

Table 71:

Compounds of the formula (III) wherein $X_3$ is heptafluoroprop-2-yl, $R_1$ is ethyl and the combination of the substituents $X_1$ and $X_2$ for each compound corresponds to a line C.1 to C.55 of Table C.

Table 72:

Compounds of the formula (III) wherein $X_3$ is heptafluoroprop-2-yl, $R_1$ is isopropyl and the combination of the substituents $X_1$ and $X_2$ for each compound corresponds to a line C.1 to C.55 of Table C.

Table 73:

Compounds of the formula (III) wherein $X_3$ is nonafluorobut-2-yl, $R_1$ is H and the combination of the substituents $X_1$ and $X_2$ for each compound corresponds to a line C.1 to C.55 of Table C.

Table 74:
  Compounds of the formula (III) wherein $X_3$ is nonafluorobut-2-yl, $R_1$ is methyl and the combination of the substituents $X_1$ and $X_2$ for each compound corresponds to a line C.1 to C.55 of Table C.

Table 75:
  Compounds of the formula (III) wherein $X_3$ is nonafluorobut-2-yl, $R_1$ is ethyl and the combination of the substituents $X_1$ and $X_2$ for each compound corresponds to a line C.1 to C.55 of Table C.

Table 76:
  Compounds of the formula (III) wherein $X_3$ is nonafluorobut-2-yl, $R_1$ is isopropyl and the combination of the substituents $X_1$ and $X_2$ for each compound corresponds to a line C.1 to C.55 of Table C.

Table 77:
  Compounds of the formula (IIIa) wherein $X_3$ is heptafluoroprop-2-yl, $R_1$ is H and the combination of the substituents $X_1$ and $X_2$ for each compound corresponds to a line C.1 to C.55 of Table C.

Table 78:
  Compounds of the formula (IIIa) wherein $X_3$ is heptafluoroprop-2-yl, $R_1$ is methyl and the combination of the substituents $X_1$ and $X_2$ for each compound corresponds to a line C.1 to C.55 of Table C.

Table 79:
  Compounds of the formula (IIIa) wherein $X_3$ is heptafluoroprop-2-yl, $R_1$ is ethyl and the combination of the substituents $X_1$ and $X_2$ for each compound corresponds to a line C.1 to C.55 of Table C.

Table 80:
  Compounds of the formula (IIIa) wherein $X_3$ is heptafluoroprop-2-yl, $R_1$ is isopropyl and the combination of the substituents $X_1$ and $X_2$ for each compound corresponds to a line C.1 to C.55 of Table C.

Table 81:
  Compounds of the formula (IIIa) wherein $X_3$ is nonafluorobut-2-yl, $R_1$ is H and the combination of the substituents $X_1$ and $X_2$ for each compound corresponds to a line C.1 to C.55 of Table C.

Table 82:
  Compounds of the formula (IIIa) wherein $X_3$ is nonafluorobut-2-yl, $R_1$ is methyl and the combination of the substituents $X_1$ and $X_2$ for each compound corresponds to a line C.1 to C.55 of Table C.

Table 83:
  Compounds of the formula (IIIa) wherein $X_3$ is nonafluorobut-2-yl, $R_1$ is ethyl and the combination of the substituents $X_1$ and $X_2$ for each compound corresponds to a line C.1 to C.55 of Table C.

Table 84:
  Compounds of the formula (IIIa) wherein $X_3$ is nonafluorobut-2-yl, $R_1$ is isopropyl and the combination of the substituents $X_1$ and $X_2$ for each compound corresponds to a line C.1 to C.55 of Table C.

Table 85:
  Compounds of the formula (III) wherein $X_3$ is 1-[chloro(difluoro)methyl]-1,2,2,2-tetrafluoro-ethyl, $R_1$ is H and the combination of the substituents $X_1$ and $X_2$ for each compound corresponds to a line C.1 to C.55 of Table C.

Table 86:
  Compounds of the formula (III) wherein $X_3$ is 1-[chloro(difluoro)methyl]-1,2,2,2-tetrafluoro-ethyl, $R_1$ is methyl and the combination of the substituents $X_1$ and $X_2$ for each compound corresponds to a line C.1 to C.55 of Table C.

Table 87:
  Compounds of the formula (III) wherein $X_3$ is 1-[chloro(difluoro)methyl]-1,2,2,2-tetrafluoro-ethyl, $R_1$ is ethyl and the combination of the substituents $X_1$ and $X_2$ for each compound corresponds to a line C.1 to C.55 of Table C.

Table 88:
  Compounds of the formula (III) wherein $X_3$ is 1-[chloro(difluoro)methyl]-1,2,2,2-tetrafluoro-ethyl, $R_1$ is isopropyl and the combination of the substituents $X_1$ and $X_2$ for each compound corresponds to a line C.1 to C.55 of Table C.

Table 89:
  Compounds of the formula (III) wherein $X_3$ is 1-[bromo(difluoro)methyl]-1,2,2,2-tetrafluoro-ethyl, $R_1$ is H and the combination of the substituents $X_1$ and $X_2$ for each compound corresponds to a line C.1 to C.55 of Table C.

Table 90:
  Compounds of the formula (III) wherein $X_3$ is 1-[bromo(difluoro)methyl]-1,2,2,2-tetrafluoro-ethyl, $R_1$ is methyl and the combination of the substituents $X_1$ and $X_2$ for each compound corresponds to a line C.1 to C.55 of Table C.

Table 91:
  Compounds of the formula (III) wherein $X_3$ is 1-[bromo(difluoro)methyl]-1,2,2,2-tetrafluoro-ethyl, $R_1$ is ethyl and the combination of the substituents $X_1$ and $X_2$ for each compound corresponds to a line C.1 to C.55 of Table C.

Table 92:
  Compounds of the formula (III) wherein $X_3$ is 1-[bromo(difluoro)methyl]-1,2,2,2-tetrafluoro-ethyl, $R_1$ is isopropyl and the combination of the substituents $X_1$ and $X_2$ for each compound corresponds to a line C.1 to C.55 of Table C.

Table 93:
  Compounds of the formula (IIIa) wherein $X_3$ is 1-[chloro(difluoro)methyl]-1,2,2,2-tetrafluoro-ethyl, $R_1$ is H and the combination of the substituents $X_1$ and $X_2$ for each compound corresponds to a line C.1 to C.55 of Table C.

Table 94:
  Compounds of the formula (IIIa) wherein $X_3$ is 1-[chloro(difluoro)methyl]-1,2,2,2-tetrafluoro-ethyl, $R_1$ is methyl and the combination of the substituents $X_1$ and $X_2$ for each compound corresponds to a line C.1 to C.55 of Table C.

Table 95:
  Compounds of the formula (IIIa) wherein $X_3$ is 1-[chloro(difluoro)methyl]-1,2,2,2-tetrafluoro-ethyl, $R_1$ is ethyl and the combination of the substituents $X_1$ and $X_2$ for each compound corresponds to a line C.1 to C.55 of Table C.

Table 96:
  Compounds of the formula (IIIa) wherein $X_3$ is 1-[chloro(difluoro)methyl]-1,2,2,2-tetrafluoro-ethyl, $R_1$ is isopropyl and the combination of the substituents $X_1$ and $X_2$ for each compound corresponds to a line C.1 to C.55 of Table C.

Table 97:
  Compounds of the formula (IIIa) wherein $X_3$ is 1-[bromo(difluoro)methyl]-1,2,2,2-tetrafluoro-ethyl, $R_1$ is H and the combination of the substituents $X_1$ and $X_2$ for each compound corresponds to a line C.1 to C.55 of Table C.

Table 98:
  Compounds of the formula (IIIa) wherein $X_3$ is 1-[bromo(difluoro)methyl]-1,2,2,2-tetrafluoro-ethyl, $R_1$ is methyl and the combination of the substituents $X_1$ and $X_2$ for each compound corresponds to a line C.1 to C.55 of Table C.

Table 99:
Compounds of the formula (IIIa) wherein $X_3$ is 1-[bromo(difluoro)methyl]-1,2,2,2-tetrafluoro-ethyl, $R_1$ is ethyl and the combination of the substituents $X_1$ and $X_2$ for each compound corresponds to a line C.1 to C.55 of Table C.

Table 100:
Compounds of the formula (IIIa) wherein $X_3$ is 1-[bromo(difluoro)methyl]-1,2,2,2-tetrafluoro-ethyl, $R_1$ is isopropyl and the combination of the substituents $X_1$ and $X_2$ for each compound corresponds to a line C.1 to C.55 of Table C.

PREPARATION EXAMPLES

Examples

The following abbreviations were used throughout this section: s=singlet; bs=broad singlet; d=doublet; dd=double doublet; dt=double triplet; t=triplet, tt=triple triplet, q=quartet, sept=septet; m=multiplet; Me=methyl; Et=ethyl; Pr=propyl; Bu=butyl; M.p.=melting point.

Example 1

Methyl 3-(ethylamino)-2-methoxy-benzoate

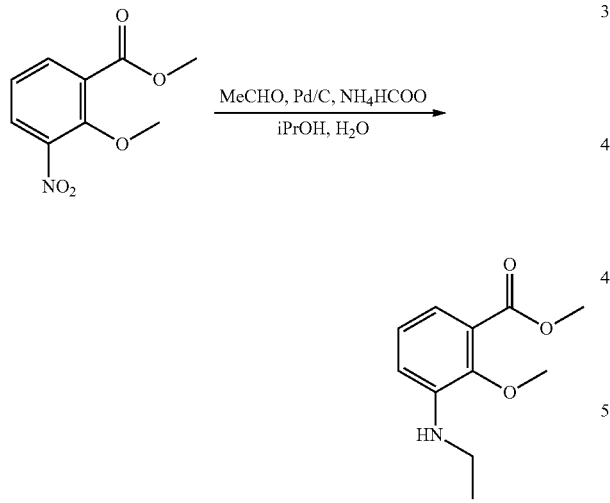

A pressure vial was charged with Pd/C (10%, 0.021 g) and 2-propanol (3.4 ml). A solution of ammonium formiate (0.452 g, 7.10 mmol) in water (0.35 ml) was added and the resulting mixture was stirred for 5 min. Methyl 2-methoxy-3-nitro-benzoate (0.100 g, 0.473 mmol) was added and the reaction media was cooled to 0 C. Acetaldehyde (0.105 g, 2.37 mmol) was added and the reaction media was stirred for 16 h at ambient temperature. The reaction mixture was filtered through a short pad of celite and filtrate was evaporated under reduced pressure. The residue was dissolved in dichloromethane and washed with brine. Organic layer was dried over anhydrous sodium sulfate and concentrated under reduced pressure. The residue was further purified by column chromatography on silica gel (eluent: 0-30% EtOAc in cyclohexane) to give methyl 3-(ethylamino)-2-methoxy-benzoate (0.0839 g, 85%) as a beige oil. $^1$H NMR (400 MHz, CDCl$_3$): 7.09 (dd, 1H), 7.01 (t, 1H), 6.77 (dd, 1H), 4.30 (bs, 1H), 3.90 (s, 3H), 3.82 (s, 3H), 3.16 (q, 2H), 1.27 (t, 3H) ppm.

Example 2

Methyl 3-[(4-cyanobenzoyl)-ethyl-amino]-2-methoxy-benzoate

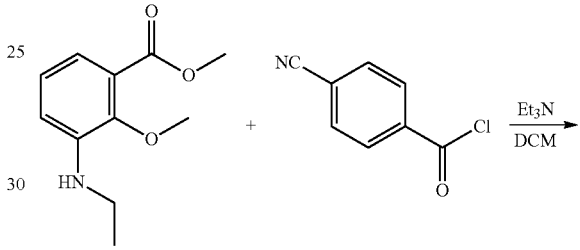

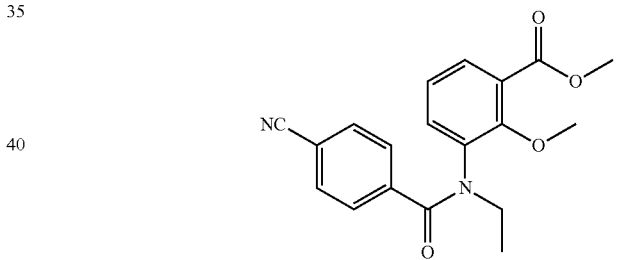

To a solution of methyl 3-(ethylamino)-2-methoxy-benzoate (0.158 g, 0.754 mmol) in dichloromethane (2.6 ml) was added triethylamine (0.233 ml, 1.66 mmol) followed by 4-cyanobenzoyl chloride (0.140 g, 0.829 mmol). After stirring at ambient temperature for 16 h the reaction was quenched by addition of saturated aqueous NH$_4$Cl. The mixture was extracted with dichloromethane (2×) and organic layers were washed with brine, dried over anhydrous sodium sulfate and evaporated under reduced pressure. The residue was further purified by column chromatography on silica gel (eluent: 0-40% EtOAc in cyclohexane) to give methyl 3-[(4-cyanobenzoyl)-ethyl-amino]-2-methoxy-benzoate (0.207 g, 81%) as a beige gum.

$^1$H NMR (400 MHz, CDCl$_3$): 7.77-7.58 (m, 1H), 7.55-7.35 (m, 4H), 7.32-7.20 (m, 1H), 7.12-6.99 (m, 1H), 4.20 (bs, 1H), 3.88 (s, 3H), 3.83 (s, 3H), 3.73-3.61 (m, 1H), 1.33-1.21 (m, 3H) ppm

Example 3

3-[(4-cyanobenzoyl)-ethyl-amino]-2-methoxy-benzoic acid

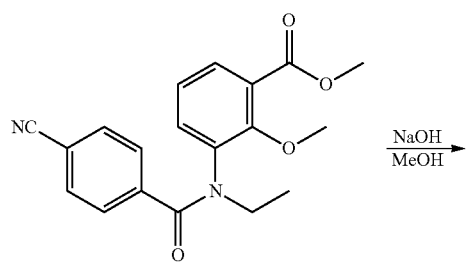

To a solution of 3-[(4-cyanobenzoyl)-ethyl-amino]-2-methoxy-benzoate (0.120 g, 0.354 mmol) in MeOH (1.2 ml) was added 5M NaOH (0.142 ml, 0.707 mmol). The reaction mixture was stirred for 1.5 h at ambient temperature before being quenched by addition of aqueous saturated NH$_4$Cl. The mixture was extracted with dichloromethane (3×), combined organic layers were washed with brine, dried over anhydrous Na$_2$SO$_4$ and concentrated under reduced pressure to obtain 3-[(4-cyanobenzoyl)-ethyl-amino]-2-methoxy-benzoic acid (0.0827 g, 72%) as a white solid sufficiently pure for further chemistry.

$^1$H NMR (400 MHz, CDCl$_3$): 7.98-7.78 (m, 1H), 7.68-7.29 (m, 5H), 7.25-7.10 (m, 1H), 4.30 (bs, 1H), 3.91 (s, 3H), 3.71-3.57 (m, 1H), 1.42-1.19 (m, 3H) ppm

Example 4

N-[2-bromo-6-chloro-4-[1,2,2,2-tetrafluoro-1-(trifluoromethyl)ethyl]phenyl]acetamide

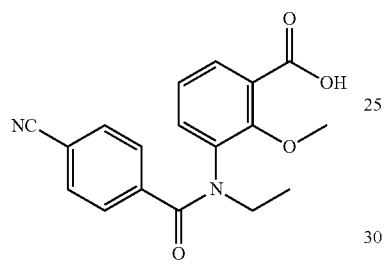

A solution of 2-bromo-6-chloro-4-[1,2,2,2-tetrafluoro-1-(trifluoromethyl)ethyl]aniline (5.00 g, 12.0 mmol) in acetic anhydride (30 ml) was heated to 60 C and few drops of concentrated sulfuric acid was added. The heating was continued for further 90 min and then most of acetic anhydride was evaporated under reduced pressure. The residue was taken dissolved in THF (25 ml) and aqueous 2N NaOH (35 ml) was added. The reaction mixture was stirred at ambient temperature for 2 h before being extracted with dichloromethane (3×). Combined organic layers were dried over anhydrous Na$_2$SO$_4$ and evaporated under reduced pressure. The crude product was purified by silica gel chromatography (0-40% EtOAc in cyclohexane) to afford N-[2-bromo-6-chloro-4-[1,2,2,2-tetrafluoro-1-(trifluoromethyl)ethyl]phenyl]acetamide (5.00 g, 90%) as a beige solid.

$^1$H NMR (400 MHz, CDCl$_3$): 7.77 (s, 1H), 7.66 (s, 1H), 7.18 (brs, 1H), 2.24 (brs, 3H) ppm.

Example 5

N-acetyl-N-[2-bromo-6-chloro-4-[1,2,2,2-tetrafluoro-1-(trifluoromethyl)ethyl]phenyl]-3-[(4-cyanobenzoyl)-ethyl-amino]-2-methoxy-benzamide Step 1

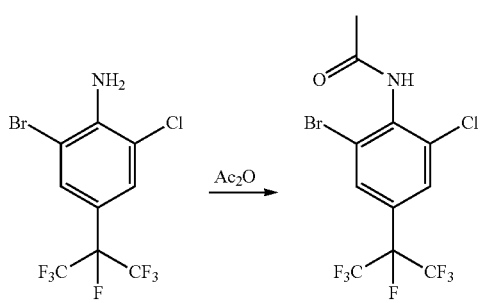 [SMILES: "Ac2O" ; Nc1c(Cl)cc(C(F)(C(F)(F)F)C(F)(F)F)cc1Br ; CC(=O)Nc1c(Cl)cc(C(F)(C(F)(F)F)C(F)(F)F)cc1Br]

Preparation of 3-[(4-cyanobenzoyl)-ethyl-amino]-2-methoxy-benzoyl chloride. To a suspension of 3-[(4-cyanobenzoyl)-ethyl-amino]-2-methoxy-benzoic acid (1.00 g, 3.08 mmol) in 1,2-dichloroethane was one drop of DMF followed by a slow addition of oxalyl chloride (0.284 ml, 3.24 mmol). The reaction mixture was stirred for further 30 min to afford a solution of 3-[(4-cyanobenzoyl)-ethyl-amino]-2-methoxy-benzoyl chloride which was used for the next step immediately.

Step 2

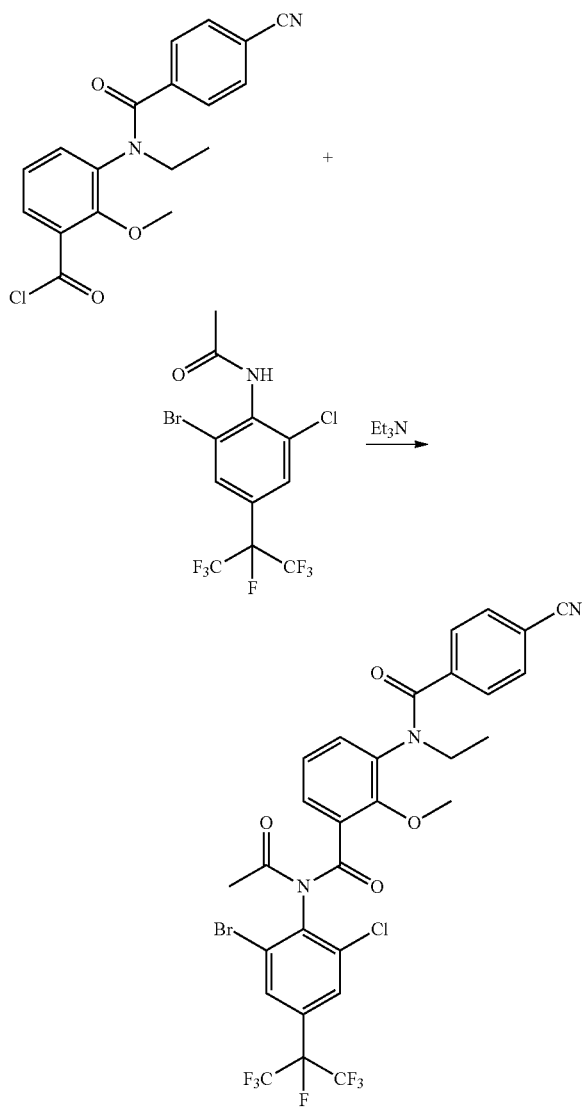

Example 6

N-[2-bromo-6-chloro-4-[1,1,1,2,3,3,3-heptafluoro-prop-2-yl]phenyl]-3-[(4-cyanobenzoyl)-ethyl-amino]-2-methoxy-benzamide

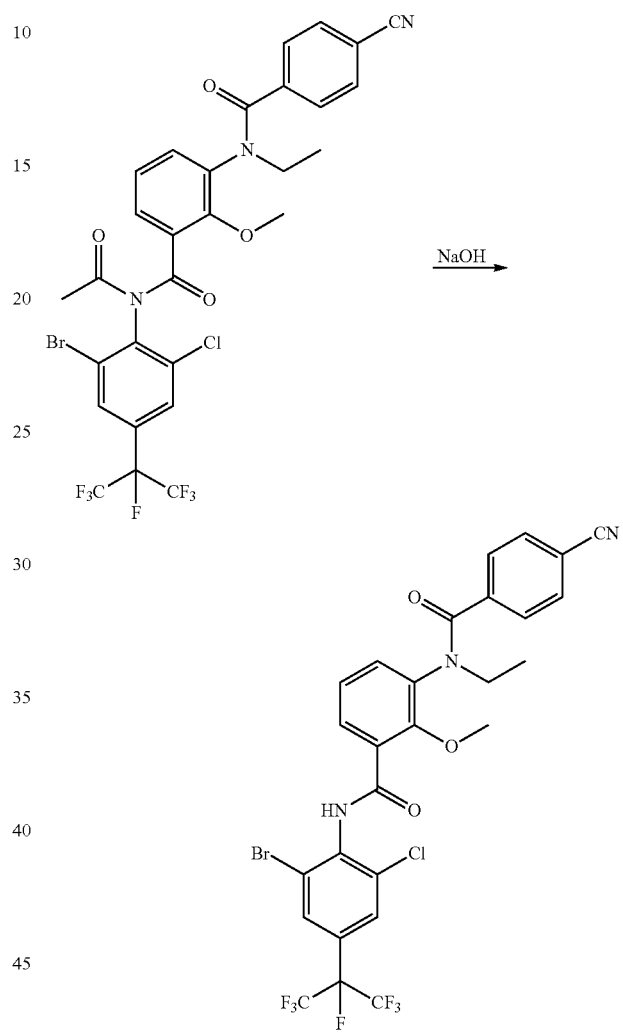

To a solution of N-[2-bromo-6-chloro-4-[1,2,2,2-tetrafluoro-1-(trifluoromethyl)ethyl]phenyl]acetamide (1.28 g, 3.08 mmol) in 1,2-dichlorethane (11 ml) was added triethylamine (1.08 ml, 7.70 mmol). The solution of acid chloride prepared in the step 1 was added dropwise at 0 C and the reaction mixture was stirred at room temperature for 4 h. The reaction was quenched by addition of aqueous saturated NaHCO3, the aqueous phase was extracted with DCM (3×), the combined organic layers were dried over anhydrous Na2SO4 and evaporated under reduced pressure. The crude product was purified by silica gel chromatography (0-30% EtOAc in cyclohexane) to afford N-acetyl-N-[2-bromo-6-chloro-4-[1,2,2,2-tetrafluoro-1-(trifluoromethyl)ethyl]phenyl]-3-[(4-cyanobenzoyl)-ethyl-amino]-2-methoxy-benzamide (1.61 g, 71%) as a white solid.

$^1$H NMR (400 MHz, CDCl$_3$): 7.88 (brs, 1H), 7.81-7.73 (m, 1H), 7.56-7.41 (m, 4H), 7.39-7.31 (m, 1H), 7.17-7.07 (m, 1H), 7.04-6.94 (m, 1H), 4.34-4.19 (m, 1H), 3.90 (s, 3H), 3.73-3.59 (m, 1H), 2.02-1.87 (m, 3H), 1.36-1.22 (m, 3H) ppm.

To a solution of N-acetyl-N-[2-bromo-6-chloro-4-[1,2,2,2-tetrafluoro-1-(trifluoromethyl)ethyl]phenyl]-3-[(4-cyanobenzoyl)-ethyl-amino]-2-methoxy-benzamide (0.0750 g, 0.0995 mmol) in THF (0.5 ml) was added 1N NaOH (0.40 ml, 0.40 mmol) and the resulting reaction mixture was stirred at room temperature for 3 h. The reaction mixture was diluted with ethyl acetate, phases were separated and the aqueous phase was extracted with ethyl acetate (2×). The combined organic layers were dried over anhydrous Na2SO4 and evaporated under reduced pressure to afford pure N-[2-bromo-6-chloro-4-[1,1,1,2,3,3,3-heptafluoroprop-2-yl]phenyl]-3-[(4-cyanobenzoyl)-ethyl-amino]-2-methoxy-benzamide (0.0706 g, 98%) as a beige solid.

$^1$H NMR (400 MHz, CDCl$_3$): 8.78 (bs, 1H), 8.04 (d, 1H), 7.81 (s, 1H), 7.70 (s, 1H), 7.55 (d, 1H), 7.40-7.55 (m, 4H), 7.43 (t, 1H), 4.34-4.48 (m, 1H), 3.96 (s, 3H), 3.67-3.80 (m, 1H), 1.48 (t, 3H) ppm.

Example 7 methyl 3-[ethyl(pyridine-4-carbonyl)amino]-2-methoxy-benzoate

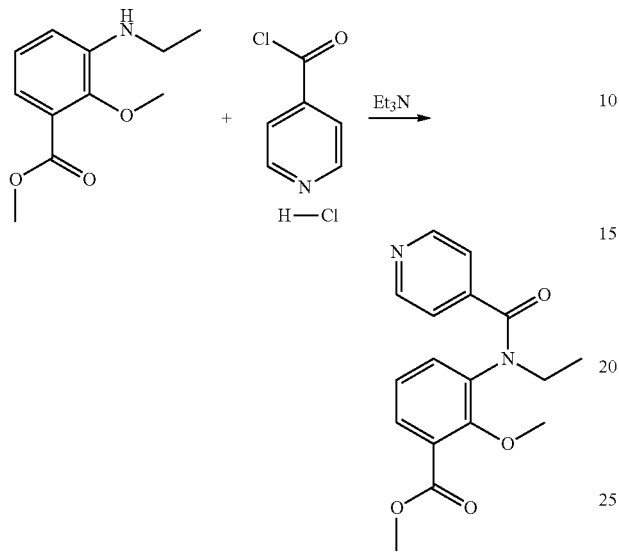

To a solution of methyl 3-(ethylamino)-2-methoxy-benzoate (1.168 g, 5.58 mmol) in DCM (20 ml) was added triethylamine (1.89 ml, 13.40 mmol) followed by isonicotinoyl chloride hydrochloride (1.217 g, 6.70 mmol) and the reaction mixture was stirred at 40 C for 1 h. The reaction mixture was cooled to room temperature and quenched by addition of aqueous saturated NaHCO₃ and 1N NaOH was added until pH=8-9. The aqueous phase was extracted with DCM (3×), combined organic layers were dried over anhydrous Na₂SO₄ and evaporated under reduced pressure. The crude product was purified by silica gel chromatography (0-100% EtOAc in cyclohexane) to afford methyl 3-[ethyl(pyridine-4-carbonyl)amino]-2-methoxy-benzoate (1.644 g, 94%) as a beige oil.

¹H NMR (400 MHz, CDCl₃): 8.44 (s, 2H), 7.65 (d, 1H), 7.30-7.11 (m, 3H), 7.09-6.98 (m, 1H), 4.31-4.17 (m, 1H), 3.88 (s, 3H), 3.84 (s, 3H), 3.71-3.59 (m, 1H), 1.33-1.23 (m, 3H) ppm.

Example 8

3-[ethyl(pyridine-4-carbonyl)amino]-2-methoxy-benzoic acid hydrochloride

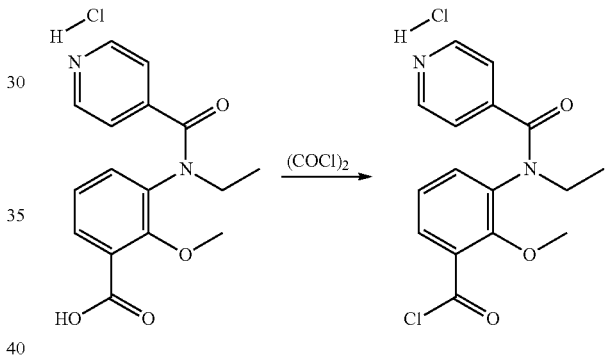

To a solution of methyl 3-[ethyl(pyridine-4-carbonyl)amino]-2-methoxy-benzoate (0.108 g, 0.343 mmol) in a mixture of THF (0.82 ml) and water (0.28 ml) was added lithium hydroxide hydrate (0.0153 g, 0.36 mmol). The reaction mixture was stirred at 50 C for 1 h, cooled to room temperature and acidified with 1N HCl. The reaction mixture was extracted with DCM (3×), the combined organic layers were dried over anhydrous Na₂SO₄ and evaporated under reduced pressure. Thus obtained crude 3-[ethyl(pyridine-4-carbonyl)amino]-2-methoxy-benzoic acid hydrochloride (0.060 g, 52%) was without further purification.

¹H NMR (400 MHz, CDCl₃): 8.48 (s, 2H), 7.89 (d, 1H), 7.43-7.32 (m, 1H), 7.27-7.09 (m, 3H), 4.38-4.24 (m, 1H), 3.92 (s, 3H), 3.70-3.58 (m, 1H), 1.40-1.27 (m, 3H) ppm.

Example 9

N-[3-[acetyl-[2-bromo-6-chloro-4-[1,2,2,2-tetrafluoro-1-(trifluoromethyl)ethyl]phenyl]carbamoyl]-2-methoxy-phenyl]-N-ethyl-pyridine-4-carboxamide Step 1

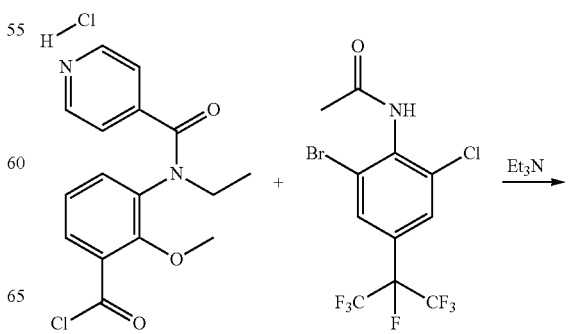

Preparation of 3-[ethyl(pyridine-4-carbonyl)amino]-2-methoxy-benzoyl chloride hydrochloride. To a suspension of 3-[ethyl(pyridine-4-carbonyl)amino]-2-methoxy-benzoic acid hydrochloride (0.0985 g, 0.278 mmol) in 1,2-dichloroethane (0.83 ml) was added one drop of DMF followed by slow addition of oxalyl chloride (0.0256 ml, 0.292 mmol). The resulting reaction mixture was stirred at room temperature for 40 min to afford a solution of 3-[ethyl(pyridine-4-carbonyl)amino]-2-methoxy-benzoyl chloride hydrochloride which was immediately used for the next step.

Step 2

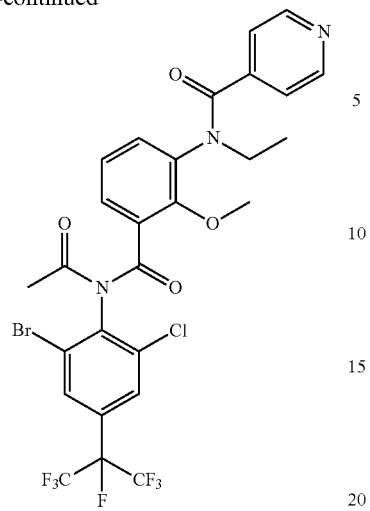

To a solution of N-[2-bromo-6-chloro-4-[1,2,2,2-tetrafluoro-1-(trifluoromethyl)ethyl]phenyl]acetamide (0.116 g, 0.278 mmol) in 1,2-dichloroethane (0.83 ml) was added triethylamine (0.137 ml, 0.973 mmol) followed by a dropwise addition of the solution of acid chloride prepared in the step 1 at 0 C. The resulting reaction mixture was stirred at room temperature for 2 h and quenched by addition of aqueous saturated NaHCO$_3$. The aqueous phase was extracted with DCM (3×), combined organic layers were dried over anhydrous Na$_2$SO$_4$ and evaporated under reduced pressure. The crude product was purified by silica gel chromatography (0-100% EtOAc in cyclohexane) to afford N-[3-[acetyl-[2-bromo-6-chloro-4-[1,2,2,2-tetrafluoro-1-(trifluoromethyl)ethyl]phenyl]carbamoyl]-2-methoxy-phenyl]-N-ethyl-pyridine-4-carboxamide (0.116 g, 59%) as a white solid.

$^1$H NMR (400 MHz, CDCl$_3$): 8.56-8.41 (m, 2H), 7.87 (s, 1H), 7.75 (d, 1H), 7.44-7.32 (m, 1H), 7.26-7.08 (m, 3H), 7.05-6.93 (m, 1H), 4.34-4.20 (m, 1H), 3.91 (s, 3H), 3.71-3.58 (m, 1H), 2.67 (d, 3H), 1.35-1.21 (m, 3H) ppm.

Example 10

N-[3-[[2-bromo-6-chloro-4-[1,2,2,2-tetrafluoro-1-(trifluoromethyl)ethyl]phenyl]carbamoyl]-2-methoxy-phenyl]-N-ethyl-pyridine-4-carboxamide

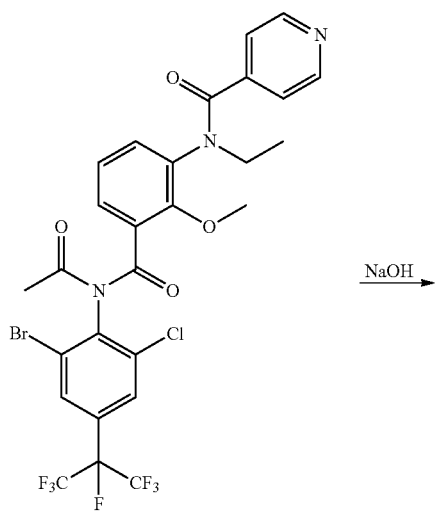

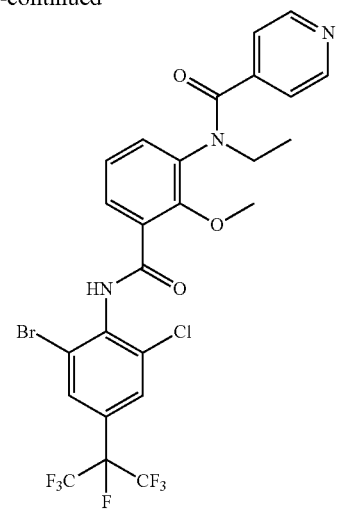

To a solution of N-[3-[acetyl-[2-bromo-6-chloro-4-[1,2,2,2-tetrafluoro-1-(trifluoromethyl)ethyl]phenyl]carbamoyl]-2-methoxy-phenyl]-N-ethyl-pyridine-4-carboxamide (0.106 g, 0.152 mmol) in THF (0.76 ml) was added 1M NaOH (0.61 ml, 0.61 mmol) and the resulting reaction mixture was stirred at room temperature for 1 h. The reaction mixture was diluted with water and ethyl acetate, phases were separated and the aqueous phase was extracted with ethyl acetate (3×). Combined organic layers were dried over anhydrous Na$_2$SO$_4$ and evaporated under reduced pressure to afford a pure N-[3-[[2-bromo-6-chloro-4-[1,2,2,2-tetrafluoro-1-(trifluoromethyl)ethyl]phenyl]carbamoyl]-2-methoxy-phenyl]-N-ethyl-pyridine-4-carboxamide (0.100 g, 96%) as a white solid.

$^1$H NMR (400 MHz, CDCl$_3$): 8.79 (s, 1H), 8.47 (s, 2H), 8.06 (d, 1H), 7.79 (s, 1H), 7.68 (s, 1H), 7.53-7.47 (m, 1H), 7.35-7.27 (m, 1H), 7.23-7.13 (m, 2H), 4.46-4.33 (m, 1H), 3.96 (s, 3H), 3.76-3.64 (m, 1H), 1.48-1.38 (m, 3H) ppm.

Example 11

N-[2-bromo-4-[1-[chloro(difluoro)methyl]-1,2,2,2-tetrafluoro-ethyl]-6-(difluoromethoxy)phenyl]acetamide

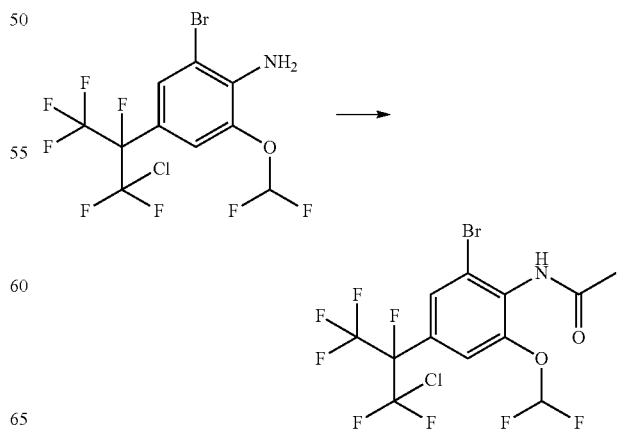

From 200 mg 2-bromo-4-[1-[chloro(difluoro)methyl]-1,2,2,2-tetrafluoro-ethyl]-6-(difluoromethoxy)aniline, following the same procedure as described in Example 4, N-[2-bromo-4-[1-[chloro(difluoro)methyl]-1,2,2,2-tetrafluoro-ethyl]-6-(difluoromethoxy)phenyl]acetamide was obtained (104 mg, 47%).

$^1$H NMR (400 MHz, CDCl$_3$): 7.77 (s, 1H), 7.48 (s, 1H), 6.93 (brs, 1H), 6.52 (t, 1H), 2.26 (s, 3H) ppm.

Example 12

2-bromo-4-[1-[chloro(difluoro)methyl]-1,2,2,2-tetrafluoro-ethyl]-6-(difluoromethoxy)aniline

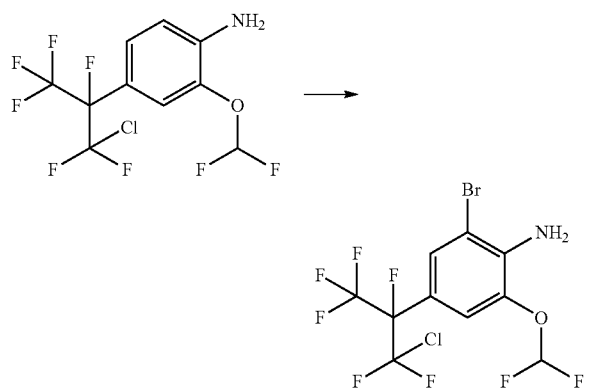

2.41 g N-bromosuccinimide was slowly added to a solution of 3.88 g 4-[1-[chloro(difluoro)methyl]-1,2,2,2-tetrafluoro-ethyl]-2-(difluoromethoxy)aniline (Example 13) in 24 ml Dichloromethane at ambient temperature. A slightly exothermic reaction was observed. The mixture was stirred for 1 hour at ambient temperature. Then 100 ml of aqueous sodium hydroxide (1N) were added. The layers were separated and the organic layer was washed with 100 ml of aqueous sodium hydroxide (1N). The aqueous phases were washed twice with 100 ml portions of dichloromethane. The combined organic layers were dried over anhydrous sodium sulfate, filtered and concentrated to dryness. Thus, 2-bromo-4-[1-[chloro(difluoro)methyl]-1,2,2,2-tetrafluoro-ethyl]-6-(difluoromethoxy)aniline (4.58 g, 96%) was obtained as a dark brown oil.

$^1$H NMR (400 MHz, CDCl$_3$): 7.55 (s, 1H), 7.24 (s, 1H), 6.50 (t, 1H), 4.60 (brs, 2H) ppm.

Example 13

4-[1-[chloro(difluoro)methyl]-1,2,2,2-tetrafluoro-ethyl]-2-(difluoromethoxy)aniline

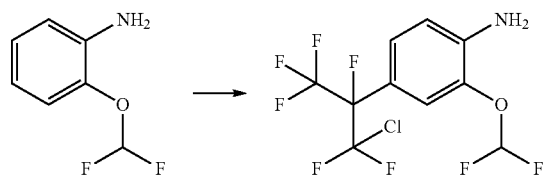 [SMILES: Nc1ccccc1OC(F)F ; Nc1ccc(C(F)(C(F)(F)F)C(F)(F)Cl)cc1OC(F)F]

6.8 g Sodium hydrosulphite, 2.8 g sodium bicarbonate, 0.69 g tetrabutylammonium hydrogensulphate and 10 g 1-chloro-1,1,2,3,3,3-hexafluoro-2-iodo-propane were added to a solution of 4.5 g 2-(difluoromethoxy)aniline in a mixture of 41 ml 2-methoxy-2-methyl-propane and 41 ml water. The reaction mixture was stirred for 3 days at ambient temperature. Then the layers were separated, the aqueous layer was washed twice with 2-methoxy-2-methyl-propane. The combined organic layers were washed twice with 100 ml portions of aqueous hyrochloric acid (1N), twice with 100 ml portions of water, once with 100 ml of brine, dried over anhydrous sodium sulfate, filtered and evaporated under vacuum. Thus, 4-[1-[chloro(difluoro)methyl]-1,2,2,2-tetrafluoro-ethyl]-2-(difluoromethoxy)aniline (3.88 g, 41%) was obtained as an orange oil.

$^1$H NMR (400 MHz, CDCl$_3$): 7.28 (m, 2H), 6.82 (d, 1H), 6.49 (t, 1H), 4.12 (brs, 2H) ppm.

Example 14

N-[2-bromo-4-[1-[chloro(difluoro)methyl]-1,2,2,2-tetrafluoro-ethyl]-6-ethyl-phenyl]acetamide

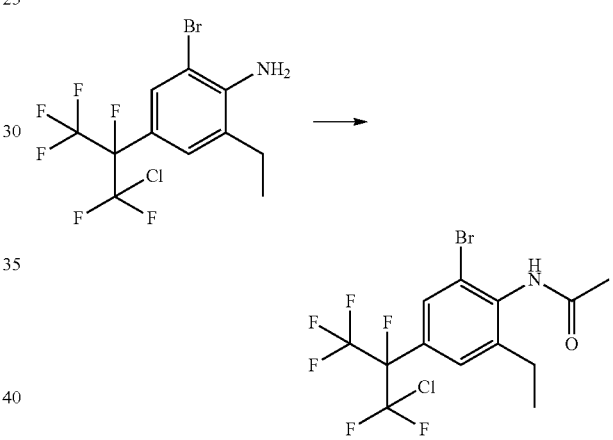

From 200 mg 2-bromo-4-[1-[chloro(difluoro)methyl]-1,2,2,2-tetrafluoro-ethyl]-6-ethyl-aniline, following the same procedure as described in Example 4, N-[2-bromo-4-[1-[chloro(difluoro)methyl]-1,2,2,2-tetrafluoro-ethyl]-6-ethyl-phenyl]acetamide was obtained (151 mg, 68%).

$^1$H NMR (400 MHz, CDCl$_3$): 7.51 (s, 1H), 7.74 (s, 1H), 6.91 (brs, 1H), 2.71 (q, 2H), 2.25 (s, 3H), 1.23 (t, 3H) ppm.

Example 15

2-bromo-4-[1-[chloro(difluoro)methyl]-1,2,2,2-tetrafluoro-ethyl]-6-ethyl-aniline

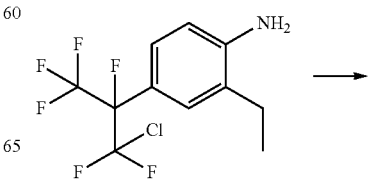

-continued

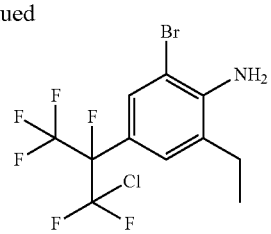

6.67 g N-bromosuccinimide was slowly added to a solution of 9.54 g 4-[1-[chloro(difluoro)methyl]-1,2,2,2-tetrafluoro-ethyl]-2-ethyl-aniline in 67 ml dichloromethane at ambient temperature. An exothermic reaction was observed. The mixture was stirred for 1.5 hours at ambient temperature. Then 100 ml of aqueous sodium hydroxide (1N) were added. The layers were separated and the organic layer was washed with 100 ml of aqueous sodium hydroxide (1N). The combined aqueous phases were washed twice with 100 ml portions of dichloromethane. The combined organic layers were dried over anhydrous sodium sulfate, filtered and concentrated to dryness. Thus, 2-bromo-4-[1-[chloro(difluoro)methyl]-1,2,2,2-tetrafluoro-ethyl]-6-ethyl-aniline (12.0 g, 100%) was obtained as a dark brown oil.

$^1$H NMR (400 MHz, CDCl$_3$): 7.53 (s, 1H), 7.20 (s, 1H), 4.38 (brs, 2H), 2.56 (q, 2H), 1.27 (t, 3H) ppm.

Example 16

4-[1-[chloro(difluoro)methyl]-1,2,2,2-tetrafluoro-ethyl]-2-ethyl-aniline

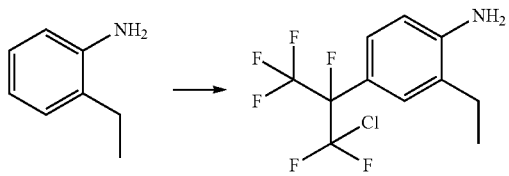

9.66 Sodium hydrosulphite, 3.96 g sodium bicarbonate, 0.97 g tetrabutylammonium hydrogensulphate and 13.5 g 1-chloro-1,1,2,3,3,3-hexafluoro-2-iodo-propane were added to a solution of 4.86 g 2-ethylaniline in a mixture of 58 ml 2-methoxy-2-methyl-propane and 58 ml water. The reaction mixture was stirred 2 hours at ambient temperature. Then the layers were separated. The aqueous layer was washed twice with 2-methoxy-2-methyl-propane. The combined organic layers were washed twice with 100 ml portions of aqueous hyrochloric acid (1N), twice with 100 ml portions of water, once with 100 ml brine, dried over sodium sulfate, filtered and evaporated under vacuum. Thus, 4-[1-[chloro(difluoro)methyl]-1,2,2,2-tetrafluoro-ethyl]-2-ethyl-aniline (9.54 g, 79%) was obtained as an orange oil.

$^1$H NMR (400 MHz, CDCl$_3$): 7.26 (m, 2H), 6.70 (d, 1H), 3.85 (brs, 2H), 2.53 (q, 2H), 1.27 (t, 3H) ppm.

Example 17

N-[2,6-dibromo-4-[1,2,2,2-tetrafluoro-1-(trifluoromethyl)ethyl]phenyl]acetamide

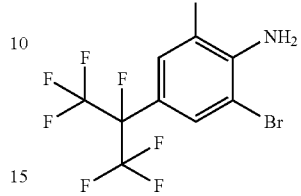

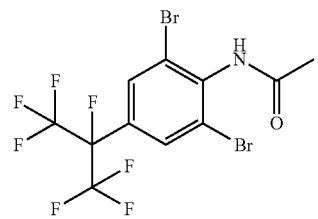

From 1.0 g 2,6-dibromo-4-[1,2,2,2-tetrafluoro-1-(trifluoromethyl)ethyl]aniline, following the same procedure as described in Example 4, N-[2,6-dibromo-4-[1,2,2,2-tetrafluoro-1-(trifluoromethyl)ethyl]phenyl]acetamide was obtained (0.98 g, 89%).

$^1$H NMR (400 MHz, CDCl$_3$): 7.82 (s, 2H), 7.00 (brs, 1H), 2.26 (brs, 3H) ppm.

Example 18

N-[2,6-diethyl-4-[1,2,2,2-tetrafluoro-1-(trifluoromethyl)ethyl]phenyl]acetamide

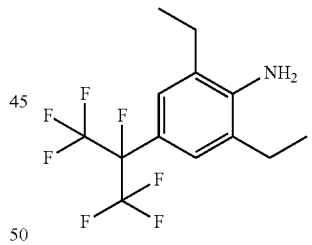

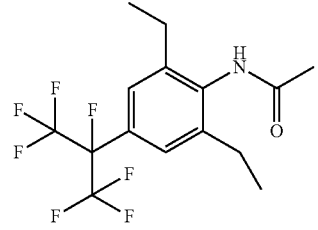

From 1.0 g 2,6-diethyl-4-[1,2,2,2-tetrafluoro-1-(trifluoromethyl)ethyl]aniline, following the same procedure as described in Example 4, N-[2,6-diethyl-4-[1,2,2,2-tetrafluoro-1-(trifluoromethyl)ethyl]phenyl]acetamide was obtained (0.93 g, 82%).

$^1$H NMR (400 MHz, CDCl$_3$): 7.33 (s, 2H), 6.70 (brs, 1H), 2.63 (q, 4H), 2.24 (s, 3H), 1.20 (t, 6H) ppm.

Example 19

N-[2-chloro-6-(difluoromethoxy)-4-[1,2,2,2-tetrafluoro-1-(trifluoromethyl)ethyl]phenyl]acetamide

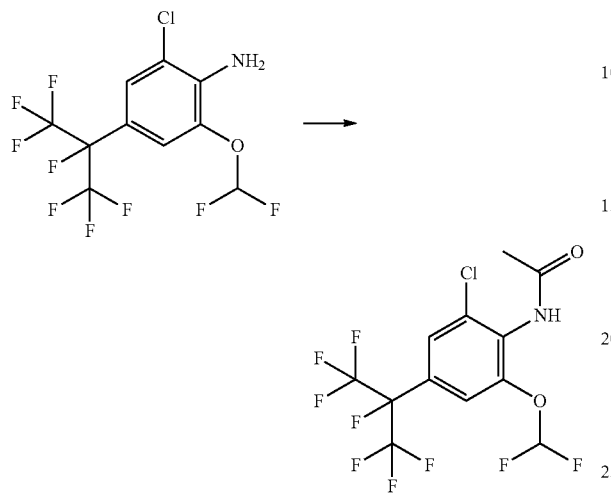

From 323 mg 2-chloro-6-(difluoromethoxy)-4-[1,2,2,2-tetrafluoro-1-(trifluoromethyl)ethyl]aniline, following the same procedure as described in Example 4, N-[2-chloro-6-(difluoromethoxy)-4-[1,2,2,2-tetrafluoro-1-(trifluoromethyl)ethyl]phenyl]acetamide was obtained (232 mg, 64%).

$^1$H NMR (400 MHz, CDCl$_3$): 7.60 (s, 1H), 7.41 (s, 1H), 6.92 (brs, 1H), 6.53 (t, 1H), 2.24 (s, 3H) ppm.

Example 20

N-[2,6-dichloro-4-[1,2,2,2-tetrafluoro-1-(trifluoromethyl)ethyl]phenyl]acetamide

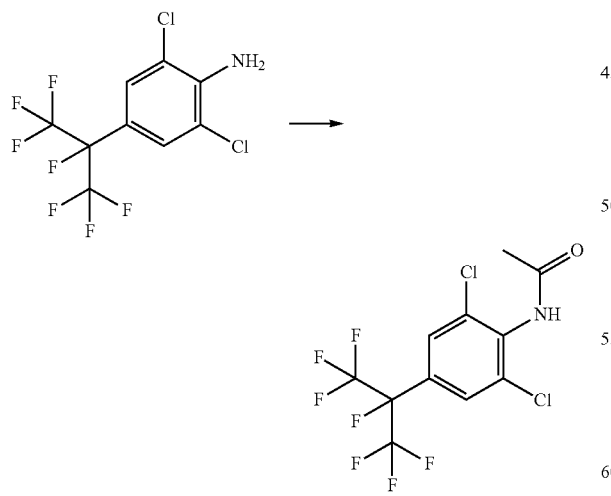

From 1.0 g 2,6-dichloro-4-[1,2,2,2-tetrafluoro-1-(trifluoromethyl)ethyl]aniline, following the same procedure as described in Example 4, N-[2,6-dichloro-4-[1,2,2,2-tetrafluoro-1-(trifluoromethyl)ethyl]phenyl]acetamide was obtained (0.296 g, 26%).

$^1$H NMR (400 MHz, CDCl$_3$): 7.62 (s, 2H), 6.95 (brs, 1H), 2.25 (brs, 3H) ppm.

Example 21

N-[2-chloro-6-methyl-4-[1,2,2,2-tetrafluoro-1-(trifluoromethyl)ethyl]phenyl]acetamide

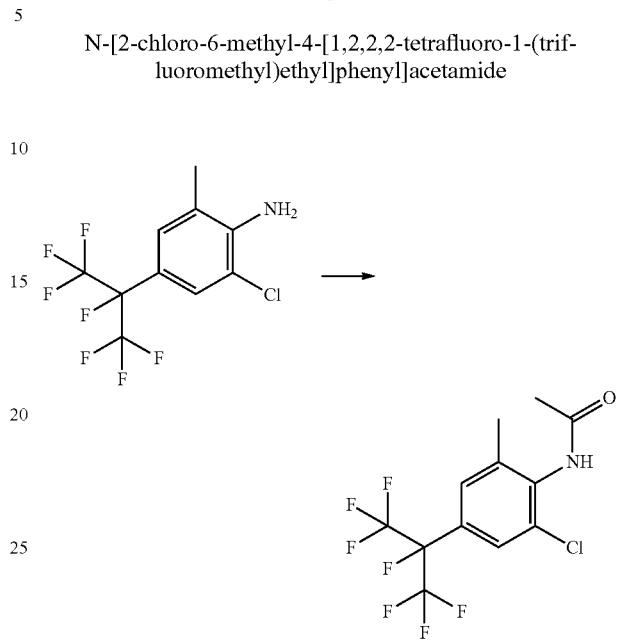

From 1.0 g 2-chloro-6-methyl-4-[1,2,2,2-tetrafluoro-1-(trifluoromethyl)ethyl]aniline, following the same procedure as described in Example 4, N-[2-chloro-6-methyl-4-[1,2,2,2-tetrafluoro-1-(trifluoromethyl)ethyl]phenyl]acetamide was obtained (1.038 g, 91%).

$^1$H NMR (400 MHz, CDCl$_3$): 7.52 (s, 1H), 7.39 (s, 1H), 6.96 ppm (brs, 1H), 2.37 (s, 3H), 2.26 (s, 3H) ppm.

Example 22

N-[2-chloro-6-ethyl-4-[1,2,2,2-tetrafluoro-1-(trifluoromethyl)ethyl]phenyl]acetamide

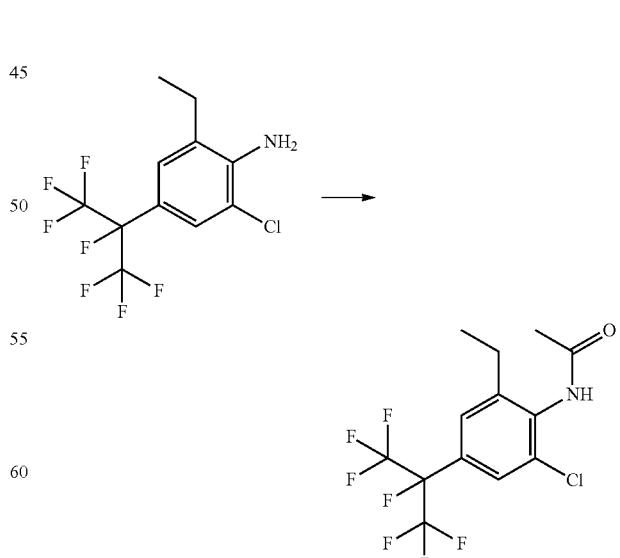

From 1.0 g 2-chloro-6-ethyl-4-[1,2,2,2-tetrafluoro-1-(trifluoromethyl)ethyl]aniline, following the same procedure as described in Example 4, N-[2-chloro-6-ethyl-4-[1,2,2,2-tetrafluoro-1-(trifluoromethyl)ethyl]phenyl]acetamide was obtained (1.1 g, 97%).

¹H NMR (400 MHz, CDCl₃): 7.54 (s, 1H), 7.42 (s, 1H), 6.88 (brs, 1H), 2.70 (q, 2H), 2.27 (s, 3H), 1.23 (t, 3H) ppm.

Example 23

2-chloro-6-ethyl-4-[1,2,2,2-tetrafluoro-1-(trifluoromethyl)ethyl]aniline

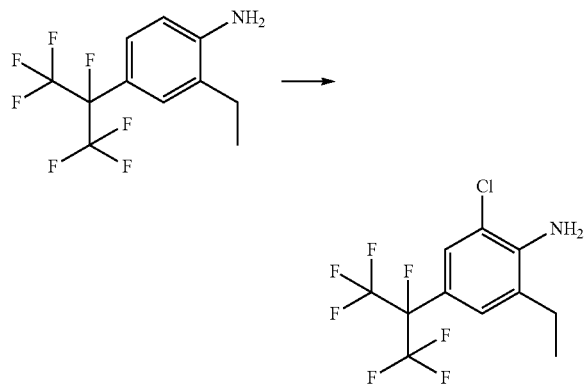

27.9 g 1-chloropyrrolidine-2,5-dione was added in portions to a solution of 60.5 g 2-ethyl-4-[1,2,2,2-tetrafluoro-1-(trifluoromethyl)ethyl]aniline in 350 ml dichloromethane. The reaction mixture was stirred for 3 days at ambient temperature. Then, 150 ml of aqueous sodium hydroxide (1N) were slowly added, during addition an exothermic reaction was observed. The layers were separated and the organic layer was washed twice with 100 ml of aqueous sodium hydroxide (1N), dried over anhydrous sodium sulfate, filtered and concentrated to dryness. The residue, 64.2 g of a dark brown powder, was purified by flash chromatography using dichloromethane/cyclohexane as a solvent. Thus, 2-chloro-6-ethyl-4-[1,2,2,2-tetrafluoro-1-(trifluoromethyl)ethyl]aniline (50.2 g, 74%) was obtained as a pale orange solid.

¹H NMR (400 MHz, CDCl₃): 7.88 (s, 1H), 7.17 (s, 1H), 4.33 brs, 2H), 2.56 (q, 2H), 1.28 (t, 3H) ppm.

Example 24

N-[2-bromo-6-ethyl-4-[1,2,2,2-tetrafluoro-1-(trifluoromethyl)ethyl]phenyl]acetamide

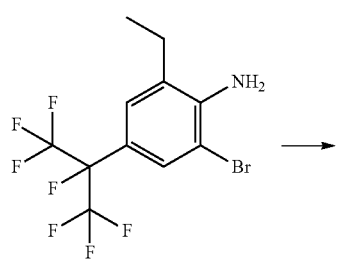

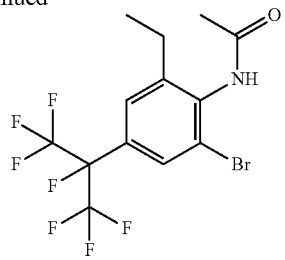

From 1.0 g 2-bromo-6-ethyl-4-[1,2,2,2-tetrafluoro-1-(trifluoromethyl)ethyl]aniline, following the same procedure as described in Example 4, N-[2-bromo-6-ethyl-4-[1,2,2,2-tetrafluoro-1-(trifluoromethyl)ethyl]phenyl]acetamide was obtained (098 g, 88%).

¹H NMR (400 MHz, CDCl₃): 7.70 (s, 1H), 7.45 (s, 1H), 6.87 (brs, 1H), 2.41 (q, 2H), 2.25 (s, 3H), 1.22 (t, 3H) ppm.

Example 25

N-[2-bromo-6-(difluoromethoxy)-4-[1,2,2,2-tetrafluoro-1-(trifluoromethyl)ethyl]phenyl]acetamide

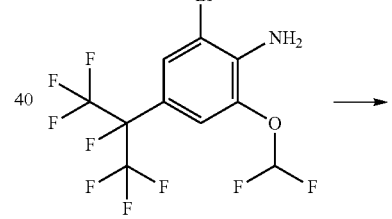

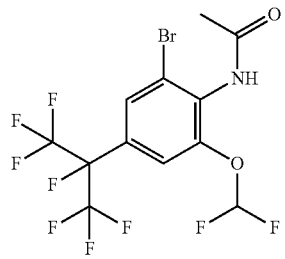

From 1.0 g 2-bromo-6-(difluoromethoxy)-4-[1,2,2,2-tetrafluoro-1-(trifluoromethyl)ethyl]aniline, following the same procedure as described in Example 4, N-[2-bromo-6-(difluoromethoxy)-4-[1,2,2,2-tetrafluoro-1-(trifluoromethyl)ethyl]phenyl]acetamide was obtained (954 mg, 86%).

¹H NMR (400 MHz, CDCl₃): 7.75 (s, 1H), 7.46 (s, 1H), 6.95 (brs, 1H), 6.52 (t, 1H), 2.24 (s, 3H) ppm.

Example 26

N-[2-bromo-4-[1-[bromo(difluoro)methyl]-1,2,2,2-tetrafluoro-ethyl]-6-ethyl-phenyl]acetamide

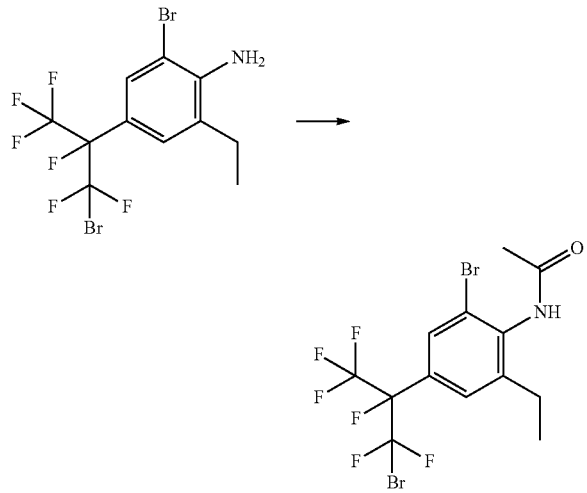

From 500 mg 2-bromo-4-[1-[bromo(difluoro)methyl]-1,2,2,2-tetrafluoro-ethyl]-6-ethyl-aniline, following the same procedure as described in Example 4, N-[2-bromo-4-[1-[bromo(difluoro)methyl]-1,2,2,2-tetrafluoro-ethyl]-6-ethyl-phenyl]acetamide was obtained (520 mg, 95%).

$^1$H NMR (400 MHz, CDCl$_3$): 7.70 (s, 1H), 7.48 (s, 1H), 7.01 (brs, 1H), 2.70 (q, 2H), 2.25 (s, 3H), 1.22 (t, 3H) ppm.

Example 27

N-[2,6-dibromo-4-[1-[bromo(difluoro)methyl]-1,2,2,2-tetrafluoro-ethyl]phenyl]acetamide

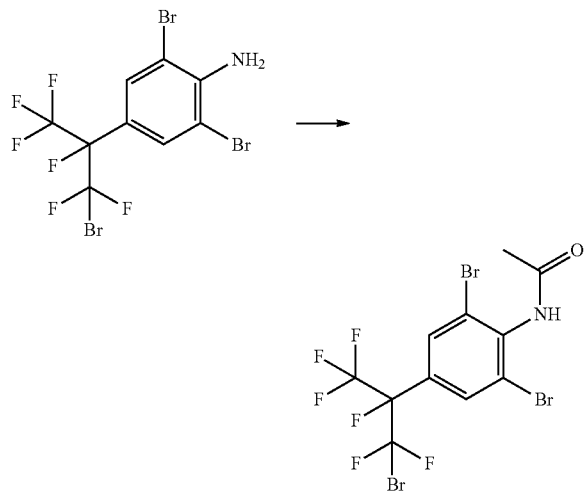

From 500 mg 2,6-dibromo-4-[1-[bromo(difluoro)methyl]-1,2,2,2-tetrafluoro-ethyl]aniline, following the same procedure as described in Example 4, N-[2,6-dibromo-4-[1-[bromo(difluoro)methyl]-1,2,2,2-tetrafluoro-ethyl]phenyl]acetamide was obtained (340 mg, 71%).

$^1$H NMR (400 MHz, CDCl$_3$): 7.84 (s, 2H), 7.01 (brs, 1H), 2.28 (s, 3H) ppm.

Example 28

N-[4-[1-[bromo(difluoro)methyl]-1,2,2,2-tetrafluoro-ethyl]-2,6-dichloro-phenyl]acetamide

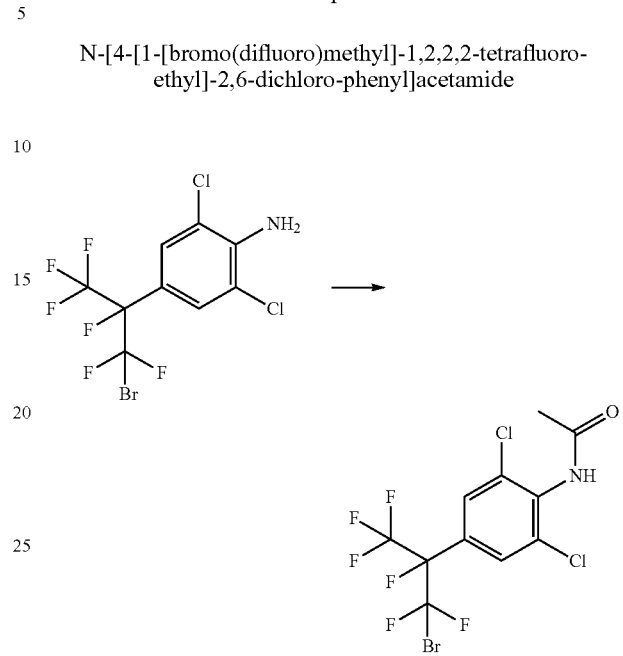

From 500 mg 4-[1-[bromo(difluoro)methyl]-1,2,2,2-tetrafluoro-ethyl]-2,6-dichloro-aniline, following the same procedure as described in Example 4, N-[4-[1-[bromo(difluoro)methyl]-1,2,2,2-tetrafluoro-ethyl]-2,6-dichloro-phenyl]acetamide was obtained (320 mg, 72%).

$^1$H NMR (400 MHz, CDCl$_3$): 7.64 (s, 2H), 6.95 (brs, 1H), 2.27 (s, 3H) ppm.

Example 29

N-[3-[acetyl-[2-bromo-6-(difluoromethoxy)-4-[1,2,2,2-tetrafluoro-1-(trifluoromethyl)ethyl]phenyl]carbamoyl]-2-methoxy-phenyl]-N-methyl-pyridine-4-carboxamide

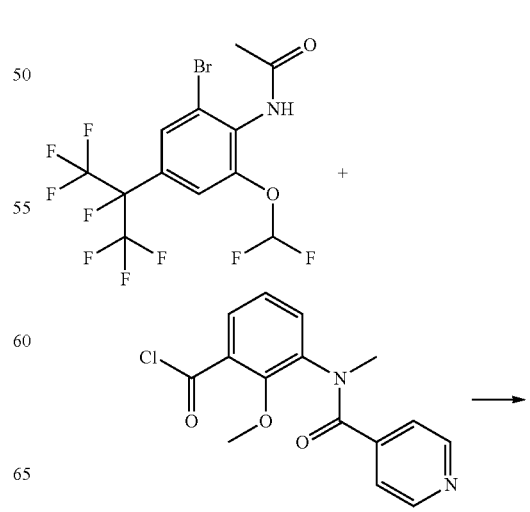

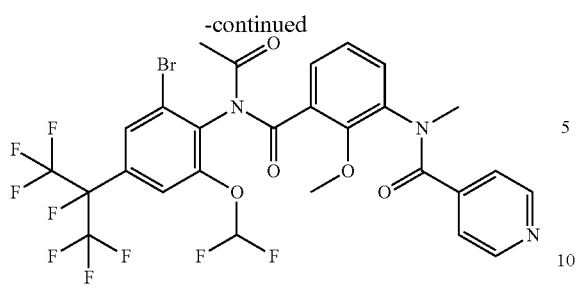

From 760 mg N-[2-bromo-6-(difluoromethoxy)-4-[1,2,2,2-tetrafluoro-1-(trifluoromethyl)ethyl]phenyl]acetamide and 520 mg 2-methoxy-3-[methyl(pyridine-4-carbonyl)amino]benzoyl chloride, following the same procedure as described in Example 5, Step 2, N-[3-[acetyl-[2-bromo-6-(difluoromethoxy)-4-[1,2,2,2-tetrafluoro-1-(trifluoromethyl)ethyl]phenyl]carbamoyl]-2-methoxy-phenyl]-N-methyl-pyridine-4-carboxamide was obtained (446 mg, 37%).

$^1$H NMR (400 MHz, CDCl$_3$): 8.50 (brs, 2H), 7.77 (m, 1H), 7.43 (brs, 1H), 7.20-7.30 (m, broad, 4H), 7.05 (m, 1H), 6.45 (t, broad, 1H), 3.88 (s, 3H), 3.43 (brs, 3H), 1.96 (brs, 3H) ppm.

Example 30

N-[3-[[2-bromo-6-(difluoromethoxy)-4-[1,2,2,2-tetrafluoro-1-(trifluoromethyl)ethyl]phenyl]carbamoyl]-2-methoxy-phenyl]-N-methyl-pyridine-4-carboxamide

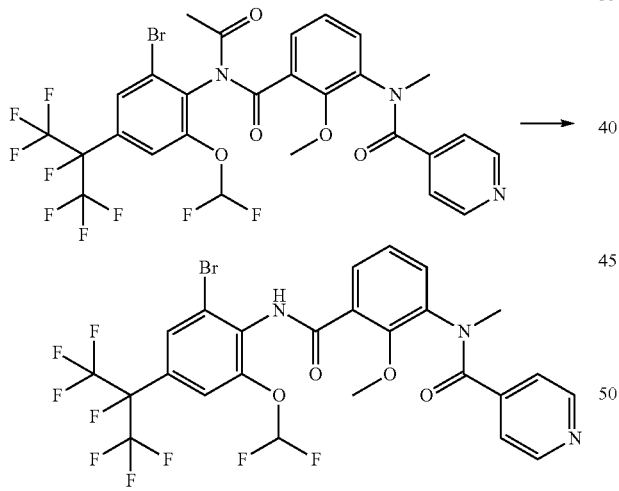

From 278 g N-[3-[acetyl-[2-bromo-6-(difluoromethoxy)-4-[1,2,2,2-tetrafluoro-1-(trifluoromethyl)ethyl]phenyl]carbamoyl]-2-methoxy-phenyl]-N-methyl-pyridine-4-carboxamide, following the same procedure as described in Example 6, N-[3-[[2-bromo-6-(difluoromethoxy)-4-[1,2,2,2-tetrafluoro-1-(trifluoromethyl)ethyl]phenyl]carbamoyl]-2-methoxy-phenyl]-N-methyl-pyridine-4-carboxamide was obtained (259 mg, 99%).

$^1$H NMR (400 MHz, CDCl$_3$): 8.73 (brs, 1H), 8.47 (brs, 2H), 8.03 (d, 1H), 7.75 (s, 1H), 7.53 (d, 1H), 7.45 (s, 1H), 7.35 (t, 1H), 7.17 (brs, 2H), 6.53 (t, 1H), 3.62 (brs, 3H), 3.58 (brs, 3H) ppm.

The invention claimed is:

1. A method for the preparation of

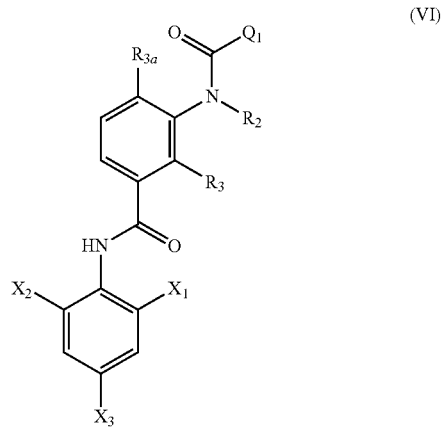

comprising reacting a compound of formula (I) with a compound of formula (II) in the presence of acid to obtain a compound of formula (III):

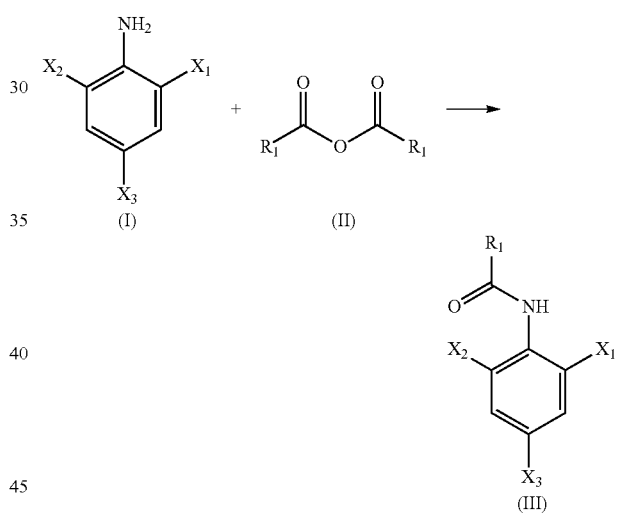

then

Step b)

reacting the compound of formula (III) with a compound of formula (IV) to obtain a compound of formula (V):

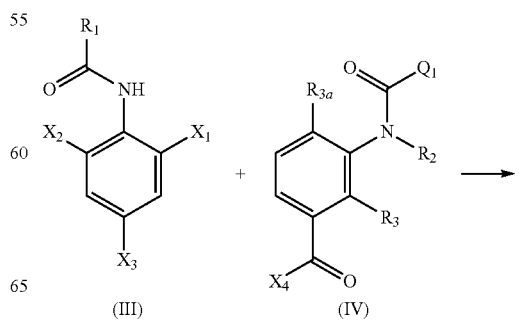

-continued

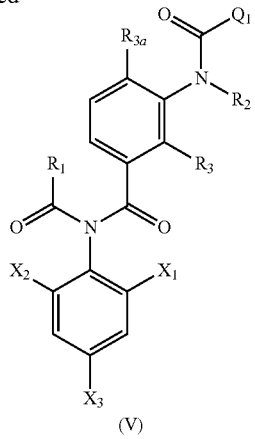

(V)

then

Step c)

reacting the compound of formula (V) with aqueous base to obtain a compound of formula (VI):

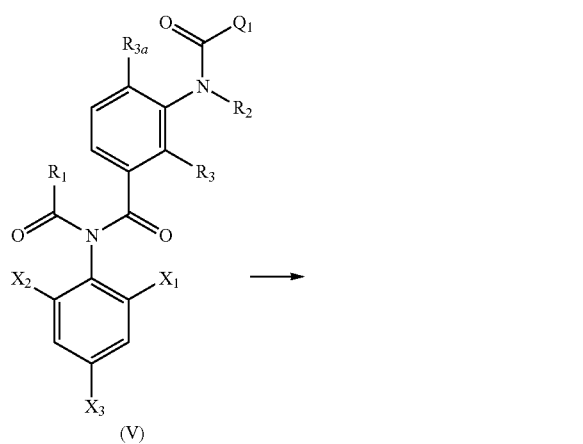

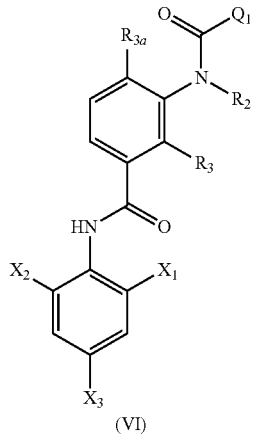

(VI)

wherein $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxymethyl, $C_1$-$C_4$-alkylsulphonyl, $C_1$-$C_4$-haloalkylsulphonyl, $C_1$-$C_4$-alkylsulphinyl, $C_1$-$C_4$-haloalkylsulphinyl, $C_1$-$C_4$-alkylthio, $C_1$-$C_4$-haloalkylthio, $X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;

$X_4$ is a leaving group selected from halogen, $C_1$-$C_6$-alkyl-C(O)O—, phenyl-C(O)O—, $C_1$-$C_6$-alkoxy-C(O)O—, phenoxy-C(O)O—, benzyloxy-C(O)O— and imidazol-1-yl;

$R_1$ is H, $C_1$-$C_4$ alkyl, $C_1$-$C_4$ haloalkyl, $R_2$ is $C_1$-$C_4$-alkyl $R_3$ is H, fluorine, methoxy;

$R_{3a}$ is H or CN, $Q_1$ is 4-cyano-phenyl, 3-pyridyl or 4-pyridyl.

2. A method according to claim 1 wherein $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxymethyl, $X_3$ is heptafluoroprop-2-yl, 1-[chloro(difluoro)methyl]-1,2,2,2-tetrafluoro-ethyl, 1-[bromo(difluoro)methyl]-1,2,2,2-tetrafluoro-ethyl or nonafluorobut-2-yl;

$X_4$ is a leaving group selected from halogen, $C_1$-$C_6$-alkyl-C(O)O—, phenyl-C(O)O—, $C_1$-$C_6$-alkoxy-C(O)O—;

$R_1$ is H, $C_1$-$C_4$ alkyl, $R_2$ is methyl or ethyl $Q_1$ is 4-cyano-phenyl, 3-pyridyl or 4-pyridyl.

3. A method according to claim 1 wherein $X_1$ and $X_2$ each independently are halogen, $C_1$-$C_4$ alkyl, $C_1$-$C_4$ haloalkyl, $C_1$-$C_4$ alkoxy, $C_1$-$C_4$ haloalkoxy, $C_1$-$C_4$ alkoxymethyl, $X_3$ is 1-[chloro(difluoro)methyl]-1,2,2,2-tetrafluoro-ethyl, 1-[bromo(difluoro)methyl]-1,2,2,2-tetrafluoro-ethyl;

$X_4$ is a leaving group selected from halogen, $C_1$-$C_6$-alkyl-C(O)O—, phenyl-C(O)O—, $C_1$-$C_6$-alkoxy-C(O)O—;

$R_1$ is H, $C_1$-$C_4$ alkyl, $R_2$ is methyl or ethyl $Q_1$ is 3-pyridyl or 4-pyridyl.

4. A method according to claim 1 wherein $X_1$ and $X_2$ each independently are halogen, $C_1$-$C_4$ alkyl, $C_1$-$C_4$ haloalkyl, $C_1$-$C_4$ haloalkoxy, $X_3$ is heptafluoroprop-2-yl;

$X_4$ is a leaving group selected from halogen, $C_1$-$C_6$-alkyl-C(O)O—;

$R_1$ is H, methyl, $R_2$ is ethyl $Q_1$ is 4-pyridyl.

5. A method according to claim 1 wherein $X_1$ and $X_2$ each independently are halogen, $C_1$-$C_4$ alkyl, $C_1$-$C_4$ haloalkyl, $C_1$-$C_4$ haloalkoxy, $X_3$ is heptafluoroprop-2-yl;

$X_4$ is a leaving group selected from halogen, $C_1$-$C_6$-alkyl-C(O)O—;

$R_1$ is H, methyl, $R_2$ is ethyl $Q_1$ is 4-pyridyl.

6. A method according to claim 1 wherein $X_1$ and $X_2$ each independently are halogen, $C_1$-$C_4$ alkyl, $C_1$-$C_4$ haloalkyl, $C_1$-$C_4$ haloalkoxy, $X_3$ is 1-[chloro(difluoro)methyl]-1,2,2,2-tetrafluoro-ethyl;

$X_4$ is a leaving group selected from halogen, $C_1$-$C_6$-alkyl-C(O)O—;

$R_1$ is H, methyl, $R_2$ is ethyl $Q_1$ is 4-pyridyl.

7. A method according to claim 1 wherein $X_1$ and $X_2$ each independently are halogen, $C_1$-$C_4$ alkyl, $C_1$-$C_4$ haloalkyl, $C_1$-$C_4$ haloalkoxy, $X_3$ is 1-[bromo(difluoro)methyl]-1,2,2,2-tetrafluoro-ethyl;

$X_4$ is a leaving group selected from halogen, $C_1$-$C_6$-alkyl-C(O)O—;
$R_1$ is H, methyl,
$R_2$ is ethyl
$Q_1$ is 4-pyridyl.

8. A method according to claim 1 wherein
$X_1$ and $X_2$ each independently are halogen, $C_1$-$C_4$ alkyl, $C_1$-$C_4$ haloalkyl, $C_1$-$C_4$ haloalkoxy,
$X_3$ is nonafluorobut-2-yl;
$X_4$ is a leaving group selected from halogen, $C_1$-$C_6$-alkyl-C(O)O—;
$R_1$ is H, methyl,
$R_2$ is ethyl
$Q_1$ is 4-pyridyl.

9. A method according to claim 1 wherein $R_3$ is methoxy and $R_{3a}$ is H.

10. A method according to claim 1 wherein $R_3$ is fluorine and $R_{3a}$ is H.

11. A method according to claim 1 wherein $R_3$ is H and $R_{3a}$ is CN.

12. A method according to claim 1 wherein $R_3$ is H and $R_{3a}$ is H.

* * * * *